(12) United States Patent
Ott et al.

(10) Patent No.: US 10,537,691 B2
(45) Date of Patent: Jan. 21, 2020

(54) SURGICAL METHOD FOR PERFORMING AN OPEN SURGICAL SITE SURGERY

(71) Applicant: Lexion Medical, LLC, St. Paul, MN (US)

(72) Inventors: Douglas E. Ott, Macon, GA (US); Nathaniel V. Tran, Apple Valley, MN (US); Steven B. Williams, White Bear Lake, MN (US); Brandon Lee Michal, White Bear Lake, MN (US)

(73) Assignee: Lexion Medical, LLC, St. Paul, MN (US)

( * ) Notice: Subject to any disclaimer, the term of this patent is extended or adjusted under 35 U.S.C. 154(b) by 1319 days.

(21) Appl. No.: 13/750,569

(22) Filed: Jan. 25, 2013

(65) Prior Publication Data
US 2013/0204180 A1   Aug. 8, 2013

Related U.S. Application Data

(60) Provisional application No. 61/591,674, filed on Jan. 27, 2012.

(51) Int. Cl.
| | | |
|---|---|---|
| A61M 13/00 | (2006.01) | |
| A61B 90/40 | (2016.01) | |
| A61G 13/10 | (2006.01) | |

(52) U.S. Cl.
CPC .......... *A61M 13/003* (2013.01); *A61M 13/00* (2013.01); *A61B 2090/401* (2016.02); *A61G 13/108* (2013.01); *A61M 2202/02* (2013.01)

(58) Field of Classification Search
CPC ........... A61B 2090/401; A61G 13/108; A61M 13/00–006; A61M 2202/02–0291
USPC ....................................................... 604/23–26
See application file for complete search history.

(56) References Cited

U.S. PATENT DOCUMENTS

| | | | | |
|---|---|---|---|---|
| 3,107,863 A | * | 10/1963 | Gennady .............. | A61G 13/108 362/149 |
| 3,881,477 A | * | 5/1975 | Von Otto ................ | A61B 90/40 128/200.24 |
| 5,411,474 A | * | 5/1995 | Ott ....................... | A61M 13/003 600/560 |

(Continued)

OTHER PUBLICATIONS

510K(k) Summary, "Pall Medical Laparoshield Conditioned Insufflation Set; K030469," 510K Notification—Cardia Innovation AB CarbonAid™ gas diffuser, Jul. 27, 2005.

(Continued)

*Primary Examiner* — Amber R Stiles
*Assistant Examiner* — Laura C Schell
(74) *Attorney, Agent, or Firm* — Baker Botts L.L.P.

(57) ABSTRACT

In accordance with one embodiment of the present disclosure, a surgical method may include making an incision in a patient. The method may also include opening the incision in order to create an open surgical site in the patient. The method may further include receiving a gas from a source. The method may further include humidifying and warming the gas received from the source. The method may further include successively reflecting the humidified and warmed gas off a plurality of non-porous surfaces within a non-porous gas delivery mechanism to create a flow. The method may further include delivering the flow of the humidified and warmed gas adjacent to or into the open surgical site.

26 Claims, 10 Drawing Sheets

(56) References Cited

U.S. PATENT DOCUMENTS

| | | | |
|---|---|---|---|
| 5,849,005 A * | 12/1998 | Garrison | A61B 17/00234 604/26 |
| 6,068,609 A | 5/2000 | Ott et al. | |
| 6,994,685 B2 | 2/2006 | Van Der Linden | |
| 7,066,902 B1 | 6/2006 | Ott et al. | |
| 2002/0128603 A1 * | 9/2002 | Booth | A61B 17/3421 604/164.01 |
| 2003/0060750 A1 | 3/2003 | Van Der Linden | |
| 2007/0088275 A1 * | 4/2007 | Stearns | A61B 17/3421 604/164.01 |
| 2010/0241061 A1 * | 9/2010 | Ott | A61B 17/3474 604/26 |
| 2010/0280436 A1 * | 11/2010 | Self | A61G 13/108 604/23 |

OTHER PUBLICATIONS

Persson, M. et al., "What Is the Optimal Device for Carbon Dioxide Deairing of the Cardiothoracic Wound and How Should It Be Positioned?" *Journal of Cardiothoracic and Vascular Anesthesia*, vol. 18, No. 2, pp. 180-184, Apr. 2004.

Persson, M. et al., "Wound Ventilation with Carbon Dioxide: A Simple Method to Prevent Direct Airborne Contamination during Cardiac Surgery?" *Journal of Hospital Infection* (2004) 56, pp. 131-136, ©2003 The Hospital Infection Society, 2004.

Persson et al., "The potential use of carbon dioxide as a carrier gas for drug delivery into open wounds," Medical Hypotheses, ©2008 Elsevier Ltd., 2008.

* cited by examiner ns, these embodiments provide advantages over porous delivery mechanisms. The non-porous surfaces may create a substantially laminar or laminar flow even in the presence of condensation.
SURGICAL METHOD FOR PERFORMING AN OPEN SURGICAL SITE SURGERY

RELATED APPLICATION

This application claims the benefit under 35 U.S.C. § 119(e) of the priority of U.S. Provisional Application No. 61/596,674 filed Jan. 27, 2012, entitled "A Surgical Method For Performing An Open Surgical Site Surgery."

TECHNICAL FIELD

This disclosure relates in general to surgical operations and more particularly to a surgical method for performing an open surgical site surgery.

BACKGROUND

Traditional methods for performing an open surgical site surgery sometimes involve providing a gas to a porous element in order to create a flow of the gas for delivery to the open surgical site. Such porous elements typically include a vast number of voids that allow the gas to pass through each void. In doing so, the voids distribute the gas in thin layers, so as to form a smooth flow. One negative to the use of such gases in a surgery is that gases are dry and have the potential to lead to various states of desiccation and tissue damage.

SUMMARY OF THE DISCLOSURE

In accordance with one embodiment of the present disclosure, a surgical method may include making an incision in a patient. The method may also include opening the incision in order to create an open surgical site in the patient, such as, for example, during a laparotomy, thoracotomy, traumatic wound procedure, cardiac or chest surgery procedure, bladder or Cesarean Section procedure, or any other open site surgery. The method may further include receiving a gas from a source. The method may further include humidifying and warming the gas received from the source. The method may further include successively reflecting the humidified and warmed gas off a plurality of non-porous surfaces within a non-porous gas delivery mechanism to create a flow. The method may further include delivering the flow of the humidified and warmed gas adjacent to or into the open surgical site.

Numerous technical advantages are provided according to various embodiments of the present disclosure. Particular embodiments of the disclosure may exhibit none, some, or all of the following advantages depending on the implementation. In certain embodiments, by successively reflecting the humidified and/or warmed gas off the plurality of non-porous surfaces, a smooth, substantially laminar, or laminar flow may be created and delivered into the open surgical site. Because condensation can clog porous delivery mechanisms, these embodiments provide advantages over porous delivery mechanisms. The non-porous surfaces may create a substantially laminar or laminar flow even in the presence of condensation.

In particular embodiments, by directing at least a portion of the condensation through one or more openings, condensation may be drained from the non-porous gas delivery mechanism, thereby further preventing the condensation from affecting the ability of the gas delivery mechanism to create a substantially laminar or laminar flow.

In certain embodiments, by delivering the flow of the humidified and/or warmed gas (which may be primarily carbon dioxide) into the open surgical site, the gas may create a space inside the open surgical site that may displace oxygen (and/or other gas, such as air) within the open surgical site. As such, the gas may significantly reduce the likelihood of embolism formation or hazard, and may also significantly reduce the infiltration of airborne pathogens or contamination in the open surgical site. Furthermore, in particular embodiments, the humidified and/or warmed gas may prevent tissues, blood vessels, and/or organs within the open surgical site from drying out. As such, less damage may occur and the tissues, blood vessels, and/or organs may behave more like their natural, homeostatic state.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following description, taken in conjunction with the accompanying drawings, in which.

DETAILED DESCRIPTION OF THE DRAWINGS

Embodiments of the present disclosure and their advantages are best understood by referring to FIGS. 1 through 9 of the drawings, like numerals being used for like and corresponding parts of the various drawings.

Figure 1:
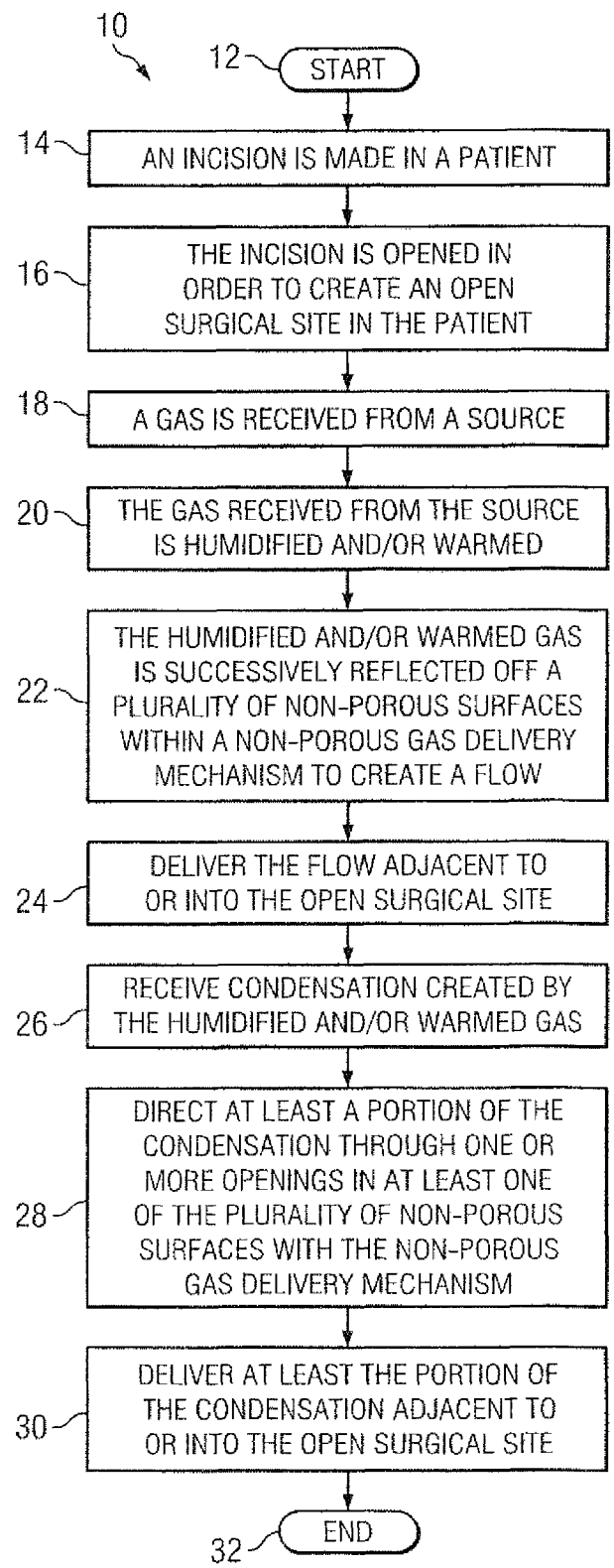
FIG. 1 illustrates one embodiment of a surgical method or performing an open surgical site surgery.

FIG. 1 illustrates one embodiment of a surgical method for performing an open surgical site surgery. In one embodiment, the surgical method 10 may include successively reflecting humidified and/or warmed gas off a plurality of non-porous surfaces within a non-porous gas delivery mechanism to create a flow. In particular embodiments, by successively reflecting the humidified and/or warmed gas off the plurality of non-porous surfaces, a smooth, substantially laminar, and/or laminar, flow may be created and delivered adjacent to or into the open surgical site As an example, successively reflecting a humidified and/or warmed gas off the plurality of non-porous surfaces may result in the Reynolds number of the gas being reduced from 1318 to 54 when the gas has a flow rate of 5 liters per minute. As another example, successively reflecting a humidified and/or warmed gas off the plurality of non-porous surfaces may result in the Reynolds number of the gas being reduced from 2500 to 115 when the gas has a flow rate of 10 liters per minute. In particular embodiments, the Reynolds number of the humidified and/or warmed gas may be reduced to any other suitable number. For example, the Reynolds number may be reduced to a number more than 54 or 115, or to a number less than 54 or 115.

Furthermore, since the plurality of non-porous surfaces are non-porous, clogging of gas flow from condensation may be reduced or eliminated as compared to the porous delivery mechanisms. As such, the non-porous gas delivery mechanism may create a smooth, substantially laminar, or laminar flow even in the presence of condensation. The surgical method 10 may further include directing at least a portion of condensation through one or more openings in at least one of the plurality of non-porous surfaces within the non-porous gas delivery mechanism. In particular embodiments, by directing at least a portion of the condensation through the one or more openings, condensation may be drained from the non-porous gas delivery mechanism, thereby further preventing the condensation from affecting the ability of the gas delivery mechanism to create a substantially laminar flow.

The method begins at step 12. At step 14, an incision is made in a patient. In one embodiment, the patient may include a human being. In another embodiment, the patient may include an animal, such as a dog, cat, horse, pig, or any other animal. The incision is made in any portion of the patient's body that may provide access to a surgical site. For example, the incision may be made in the head of the patient, a limb of the patient, the abdomen of the patient, the chest of the patient, or any other area of the patient. In particular embodiments, the incision may be made in the patient in order to conduct an open surgical site surgery in the patient. An open surgical site surgery may refer to any surgery where an inner portion of the patient is uncovered in order to perform a surgical method. Example open site surgeries may include laparotomy, thoracotomy, traumatic wound procedures, cardiac or chest surgery procedures, bladder or Cesarean Section procedures, or any other open site surgery. The incision may be made with any instrument. For example, the incision may be made with a scalpel, knife, needle, or any other instrument.

At step 16, the incision is opened in order to create an open surgical site in the patient. An open surgical site may refer to any surgical site where an inner portion of the patient is uncovered so as to perform a surgical method. For example, an open surgical site may include a surgical void in the patient that is open and exposed to the environment where the surgery is occurring.

The incision may be opened in any manner so as to create the open surgical site in the patient. For example, opening the incision to create the open surgical site may include any number of additional incisions and/or dissections of the patient's skin, tissues, muscles, blood vessels, organs, and/or bones. Furthermore, opening the incision to create the open surgical site may also include clamping one or more blood vessels to prevent bleeding and/or inserting any number of surgical instruments (such as, for example, a retractor) to expose the open surgical site to the environment and/or keep the incision open. The incision may be made opened with any instrument. For example, the incision may be opened with a scalpel, knife, saw, needle, clamp, retractor, or any other instrument.

At step 18, a gas is received from a source. The gas may include any suitable gas. For example, the gas may include carbon dioxide, oxygen, nitrous oxide, argon, helium, nitrogen, room air, or inert gases. In a further embodiment, the gas may include a combination of gases. For example, the gas may include a combination of carbon dioxide and nitrous oxide. Often the gas will be one, such as carbon dioxide, that reduces embolism risk. In particular embodiments, the gas may be received at any suitable apparatus. For example, in one embodiment, the gas may be received at the apparatus 100, as is described in FIG. 4 In another embodiment, the gas may be received from any suitable source. For example, the gas may be received from the insufflator 104, as is described in FIG. 4 As another example, the gas may be received from any other source that may provide a gas, such as, for example, a gas cartridge, a gas pump, a tank with a flow regulator, a centralized gas supply system in a hospital, or any other suitable gas source.

At step 20, the gas received from the source may be humidified and/or warmed. In one embodiment, the gas may be humidified and/or warmed by passing the gas through a chamber comprising a volume of a liquid. For example, the gas may be passed through the heater/humidifier 120, as is described in FIG. 5 As another example, the gas may be passed through any other suitable heater/humidifier. In another embodiment, the gas may be warmed to any particular temperature. For example, the temperature of the gas may be warmed so that it is within a temperature range as it exits the heating/humidifying chamber for delivery adjacent to or into the open surgical site. In one embodiment, the temperature range that the gas is warmed to is approximately 35°-40° C. For example, the gas may be warmed using a predetermined temperature set point, such as, 37° C. Other set points could be used without departing from the scope of the invention. Warming to a set point may result in a temperature range at the exit of the chamber. In another embodiment, the temperature that the gas is warmed to may be below 35° C. In a further embodiment, the temperature that the gas is warmed to may be above 40° C. In particular embodiments, the temperature range that the gas is warmed to may be approximately 28°-33° C., 30°-35° C., 32°-37° C., 37°-42° C., 39°-44° C., or any other suitable temperature range. In particular embodiments, the gas does not always need be warmed to a particular temperature range. For example, changes in the flow conditions or other influences may cause the temperature of the gas to be outside of the temperature range for a period of time. In some embodiments, the temperature may be adjustable and in others it may not.

The gas may be humidified to any particular relative humidity. For example, the gas may be humidified so that it is within a range of relative humidity at the exit of the heater/humidifier for delivery adjacent to or into the open surgical site of the patient. It may also be within any of the following humidity ranges as the gas enters the patient through the exit of a delivery device. The relative humidity level may be above 40%, above 50%, above 60%, above 70%, above 75%, above 80%, above 85%, or above 90% relative humidity. In further embodiments, the range of relative humidity may be between 65-80%, between 70-85%, between 75-90%, between 80-95%, or any other suitable range. In particular embodiments, the relative humidity of the gas does not always need to be within a particular range of relative humidity. For example, changes in the flow conditions or other influences may cause the relative humidity of the gas to be outside of the range of relative humidity for a period of time. In some embodiments, the relative humidity may be between 95% and 100%.

According to particular embodiments, the method may further include monitoring the relative humidity of the humidified gas. For example, in one embodiment, if the relative humidity of the gas falls below a predetermined relative humidity threshold, a signal may alert a user about the drop in relative humidity. In one embodiment, the method may further include injecting an additional amount of the liquid into the chamber. For example, the liquid may be injected into the chamber 128, as is discussed in FIG. 5 As such, in one embodiment, the additional amount of the liquid may increase the relative humidity of the gas.

In one embodiment, the liquid used to humidify the gas may include any suitable liquid. For example, the liquid may include water, such as sterile water. As another example, the liquid may include saline. In a further embodiment the liquid may include an anesthetic, antibiotic, or both. For example, the liquid may include lidocaine. In a further embodiment, the liquid may include an anticoagulant in order to prevent blood clots or clotting. For example, the liquid may include heparin or Angiomax. In a further embodiment, the liquid may include any other medicant or pharmacologic agent. The liquid may also include a combination of water (or saline) and other substances, such as anesthetics, antibiotics, or anticoagulants. In a further embodiment, the liquid may include a gel substance containing water and other substances. In particular embodiments, the volume of the liquid may be contained in an absorbent material, such as is discussed in FIG. 5 In a further embodiment, the volume of the liquid may be maintained between two or more membranes, such as is also discussed in FIG. 5.

The method may further include filtering the gas received from the source. The filtering of the gas may be performed by any suitable filter. For example, the filtering of the gas may be accomplished using the filter 110 of FIG. 4 The gas may be filtered prior to the gas being humidified and/or warmed. The gas may be filtered after being humidified and/or warmed. In an additional embodiment, the gas may be filtered at any time before the humidified and/or warmed gas is delivered adjacent to or into the open surgical site.

In the illustrated embodiment, gas is both humidified and warmed. However, in some embodiments, the gas may only be humidified, while in others it may only be warmed. Warming may use any type of heater, while humidification may involve a volume of water in the chamber where the gas flows without use of a heater.

At step 22, the humidified and/or warmed gas is successively reflected off a plurality of non-porous surfaces within a non-porous gas delivery mechanism to create a flow. Reflection of the humidified and/or warmed gas may refer to any change of direction that causes the humidified and/or warmed gas to flow towards either another non-porous surface or the open surgical site. Furthermore, successive reflections may refer to two or more reflections, where the final reflection causes the humidified and/or warmed gas to flow towards the open surgical site in a smooth, substantially laminar, or laminar flow.

The humidified and/or warmed gas may be successively reflected off any number of non-porous surfaces within the non-porous gas delivery mechanism. For example, the humidified and/or warmed gas may be successively reflected off of two non-porous surfaces, three non-porous surfaces, four non-porous surfaces, six non-porous surfaces, ten non-porous surfaces, or any other number of non-porous surfaces within the non-porous gas delivery mechanism.

As is discussed above, each reflection of the humidified and/or warmed gas may cause the humidified and/or warmed gas to either be reflected towards another non-porous surface within the non-porous gas delivery mechanism or reflected toward the open surgical site. For example, the humidified and/or warmed gas may be directed to a first non-porous surface within the non-porous gas delivery mechanism, and the first non-porous surface may reflect the humidified and/or warmed gas towards a second non-porous surface within the non-porous gas delivery mechanism. The second non-porous surface may then reflect the humidified and/or warmed gas towards an outlet of the non-porous gas delivery mechanism (so as to be delivered adjacent to or into the open surgical site). Alternatively, instead of reflecting the humidified and/or warmed gas towards the outlet of the non-porous gas delivery mechanism, the second non-porous surface may reflect the humidified and/or warmed gas to a third non-porous surface within the non-porous delivery mechanism. The third non-porous surface may then reflect the humidified and/or warmed gas towards a fourth non-porous surface within the non-porous gas delivery mechanism. Furthermore, the fourth non-porous surface may then reflect the humidified and/or warmed gas towards an outlet of the non-porous gas delivery mechanism (so as to be delivered adjacent to or into the open surgical site). However, in particular embodiments, instead of reflecting the humidified and/or warmed gas towards outlet of the non-porous gas delivery mechanism, the fourth non-porous surface may reflect the humidified and/or warmed gas towards an additional non-porous surface within the non-porous gas delivery mechanism so as to continue the successive reflection of the humidified and/or warmed gas for any number of times until the humidified and/or warmed gas is reflected towards an outlet of the non-porous gas delivery mechanism (so as to be delivered adjacent to or into the open surgical site).

Successively reflecting the humidified and/or warmed gas off the plurality of non-porous surfaces may create a flow of the humidified and/or warmed gas. For example, successively reflecting the humidified and/or warmed gas off the plurality of non-porous surfaces may create a smooth, substantially laminar, or laminar flow. A substantially laminar flow may refer to any flow that includes little to no turbulence. As such, a substantially laminar flow may be partially turbulent, but the majority of the flow may be laminar. In particular embodiments, a substantially laminar flow may include any flow that may allow an environment of the humidified and/or warmed gas to be created in the open surgical site. As another example, successively reflecting the humidified and/or warmed gas off the plurality of non-porous surfaces may create a flow of the humidified and/or warmed gas that has less velocity than a flow of the humidified and/or warmed gas that is initially directed to the first non-porous surface within the non-porous gas delivery mechanism. In particular, if the flow of the humidified and/or warmed gas that is initially directed towards the first non-porous surface has, for example, a flow rate of five liters per minute, the flow created by the successive reflection of the humidified and/or warmed gas may have a flow rate that is less than five liters per minute, such as, for example, four liters per minute, three liters per minute, two liters per minute, or any other flow rate. In particular embodiments, each reflection of the humidified and/or warmed gas off of a non-porous surface may decrease the flow rate of the humidified and/or warmed gas.

The successive reflection of the humidified and/or warmed gas may be performed using any type of non-porous surfaces within any type of non-porous gas delivery mechanism. For example, the non-porous gas delivery mechanism where the successive reflections are performed may include any non-porous gas delivery mechanism that includes two or more non-porous surfaces. In particular embodiments, the non-porous gas delivery mechanism and/or non-porous surfaces may include the non-porous gas delivery mechanisms and/or non-porous surfaces discussed with regard to FIGS. 2A-2C and/or FIG. 2D-2E. In particular embodiments, the non-porous gas delivery mechanism and/or non-porous surfaces may include any other non-porous gas delivery mechanism and/or non-porous surfaces.

The non-porous gas delivery mechanism and non-porous surfaces may have any size and/or shape. Furthermore, the non-porous gas delivery mechanism and non-porous surfaces may be made of any non-porous material type. A non-porous material may generally refer to a non-absorbent, solid material that reflects humidified and/or warmed gas. Although a non-porous material may be porous to certain elements, the non-porous material may not be porous to the humidified and/or warmed gas. As such, instead of allowing the humidified and/or warmed gas to pass through the non-porous material, the non-porous material may cause the humidified and/or warmed gas to reflect off the non-porous material. Non-porous materials may include, for example but not by way of limitation, plastic, acrylic, injection molded plastic, and Acrylonitrile butadiene styrene (ABS). A non-porous material is not intended to refer to porous, absorbable materials, such as a sponge.

At step 24, the flow is delivered adjacent to or into the open surgical site. In particular embodiments, the flow may include the flow of humidified and/or warmed gas created by successively reflecting the humidified and/or warmed gas, as is discussed above. The flow may be delivered adjacent to or into the open surgical site using any device. For example, the flow may be delivered adjacent to or into the open surgical site using a non-porous gas delivery mechanism, such as the non-porous gas delivery mechanisms described with regard to FIGS. 2A-2C and/or FIGS. 2D-2E. As another example, the flow may be delivered adjacent to or into the open surgical site using any other device. For example, in particular embodiments, a secondary delivery device may be attached to the non-porous gas delivery mechanisms described with regard to FIGS. 2A-2C and/or FIGS. 2D-2E.

In particular embodiments, by delivering the flow of the humidified and/or warmed gas to the vicinity of the open surgical site, the gas may create a space, such as a pocket or an environment, inside of the open surgical site and/or above it or surrounding it that contains a portion of the warmed and/or humidified gas. In particular embodiments, the portion of the humidified and/or warmed gas delivered to the open surgical site may displace oxygen (and/or other gas, such as air) within or around the open surgical site. As such, the humidified and/or warmed gas may significantly reduce the likelihood of serious embolism formation. Furthermore, the humidified and/or warmed gas may also significantly reduce the infiltration of airborne pathogens in the open surgical site. Furthermore, in particular embodiments, the humidified and/or warmed gas may prevent tissues, blood vessels, and/or organs within or around the open surgical site from drying out or reduce the rate of drying out. As such, less damage may occur and the tissues, blood vessels, and/or organs may behave more towards their natural, homeostatic state.

In particular embodiments, delivering the flow adjacent to or into the open surgical site may include positioning the delivery device (such as the non-porous gas delivery mechanism) adjacent to or within the surgical site. For example, during the open surgical site surgery, the non-porous gas delivery mechanism may be inserted into the open surgical site so that the flow of the gas may create a space of the gas in the open surgical site. As another example, during the open surgical site surgery, the non-porous gas delivery mechanism may be located outside of the open surgical site in such a way that the flow of the gas may still create a space of the gas in the open surgical site. The non-porous gas delivery mechanism may be located outside of the open surgical site in any manner. For example, the non-porous gas delivery mechanism may be held (and otherwise kept positioned) outside of the open surgical site by a person or a device, such as the adjustable arm support described with regard to FIG. 3.

At step 26, condensation created by the humidified and/or warmed gas may be received. The condensation may be received by the non-porous gas delivery mechanism. For example, the condensation may be received by the non-porous gas delivery mechanisms described with regard to FIGS. 2A-2C and/or FIGS. 2D-2E. In particular embodiments, the received condensation may have been created when a portion of the humidified and/or warmed gas is cooled, such as when a portion of the humidified and/or warmed gas touches a cooler surface. In particular embodiments, the received condensation may have been created in any other manner.

At step 28, at least a portion of the condensation is directed through one or more openings in at least one of the plurality of non-porous surfaces within the non-porous gas delivery mechanism. The portion of the condensation that is directed through the openings may include any amount of the condensation. For example, it may include all of the condensation or a lesser amount of the condensation. In particular embodiments, condensation may be directed through one or more openings by the shape, configuration, and/or placement of the non-porous surfaces and/or the flow rate of the humidified and/or warmed gas. For example, if the shape of the non-porous surfaces is curved, the curvature may cause the condensation to move towards and through the openings in the non-porous surfaces. As another example, the flow rate of the humidified and/or warmed gas may force the condensation towards and through the openings in the non-porous surfaces.

The non-porous surfaces within the non-porous gas delivery mechanism may include any number of openings. For example, the non-porous surfaces may include one opening, two openings, three openings, four openings, five openings, or any other number of openings. Furthermore, each non-porous surface within the non-porous gas delivery system may include a different number of openings. For example, while one non-porous surface may include three openings, another non-porous surface may include zero openings, one opening, two openings, four openings, or any other number of openings. Additionally, the openings may have any size and/or shape, and may be located at any location in the non-porous surfaces. In particular embodiments, the openings may include any of the openings described with regard to FIGS. 2A-2C and/or FIGS. 2D-2E.

In particular embodiments, by directing at least the portion of the condensation through the one or more openings, condensation may be drained from the non-porous gas delivery mechanism. Therefore, the condensation build-up is reduced in the non-porous gas delivery mechanism and may reduce or prevent clogging of the non-porous delivery mechanism such that there is no material impeding of gas flow. In particular embodiments, this may prevent or reduce the effect of condensation on the successive reflections of the humidified and/or warmed gas. As such, the non-porous gas delivery mechanism may continue to create a smooth, substantially laminar, or laminar flow despite the fact that the non-porous gas delivery mechanism may receive condensation.

At step 30, at least the portion of the condensation is delivered adjacent to or into the open surgical site. The condensation may be delivered adjacent to or into the open surgical site using any device. For example, the condensation may be delivered adjacent to or into the open surgical site using a non-porous gas delivery mechanism, such as the non-porous gas delivery mechanisms described with regard to FIGS. 2A-2C and/or FIGS. 2D-2E. As another example, the condensation may be delivered adjacent to or into the open surgical site using any other device. For example, in particular embodiments, a secondary delivery device may be attached to the non-porous gas delivery mechanisms described with regard to FIGS. 2A-2C and/or FIGS. 2D-2E.

In particular embodiments, by delivering the condensation adjacent to or into the open surgical site, the condensation may be drained from the non-porous gas delivery mechanism. Therefore, some embodiments may reduce the build-up of condensation in the non-porous gas delivery mechanism and/or reduce clogging of the non-porous delivery mechanism. In particular embodiments, this may prevent the condensation from materially affecting the successive reflections of the humidified and/or warmed gas. As such, the non-porous gas delivery mechanism may continue to create a smooth, substantially laminar, or laminar flow despite the fact that the non-porous gas delivery mechanism may receive condensation.

At step 32, the surgical method 10 ends. As is discussed above, in one embodiment, the surgical method 10 may allow a humidified and/or warmed gas to be delivered adjacent to or into the open surgical site. As such, surgical method 10 may allow the patient to receive the benefits of a humidified and/or warmed gas, without forcing the surgical team to deal with a porous element that may become clogged due to the condensation.

The steps illustrated in FIG. 1 may be combined, modified, or deleted where appropriate. Additional steps may also be added to the example given. Furthermore, the described steps may be performed in any suitable order. For example, certain steps may be performed in parallel with other steps. In particular, steps 26-30 may be performed in parallel with steps 22-24 of method 10.

As is discussed above, FIG. 1 illustrates one embodiment of a surgical method for performing an open surgical site surgery. FIGS. 2-9, on the other hand, illustrate particular embodiments of one or more apparatuses that may be used during the method of FIG. 1. Although FIGS. 2-9 illustrate particular embodiments of one or more apparatuses that may be used in the method of FIG. 1, any other suitable apparatuses may be used in the method. For example, any suitable apparatus may be used to humidify and/or warm the gas of the method of FIG. 1.

Figure 2B:
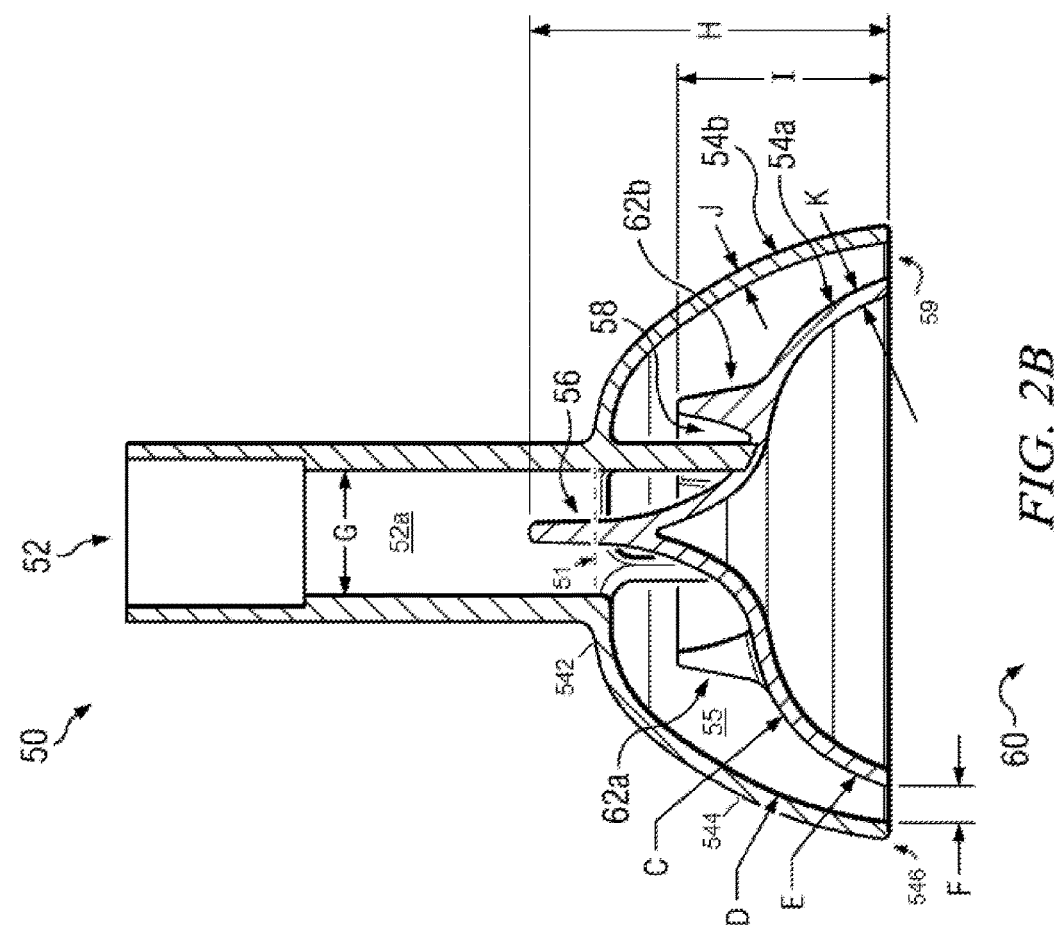
FIGS. 2A-2E illustrate example embodiments of a non-porous gas delivery mechanism that may be used in a surgical method.
Figure 2A:
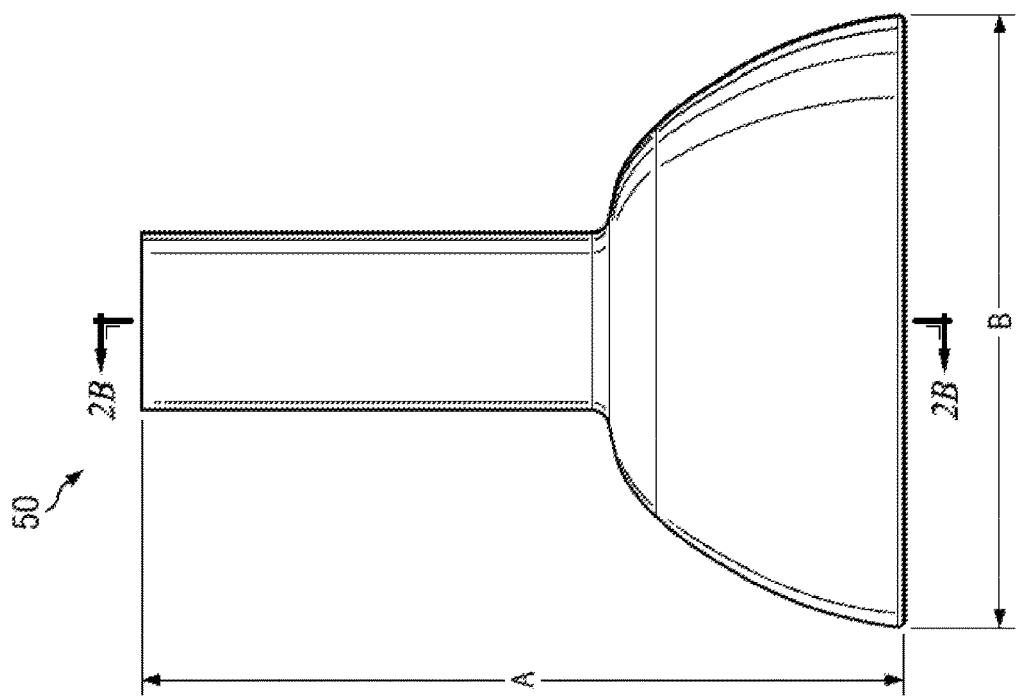
Figure 2C:
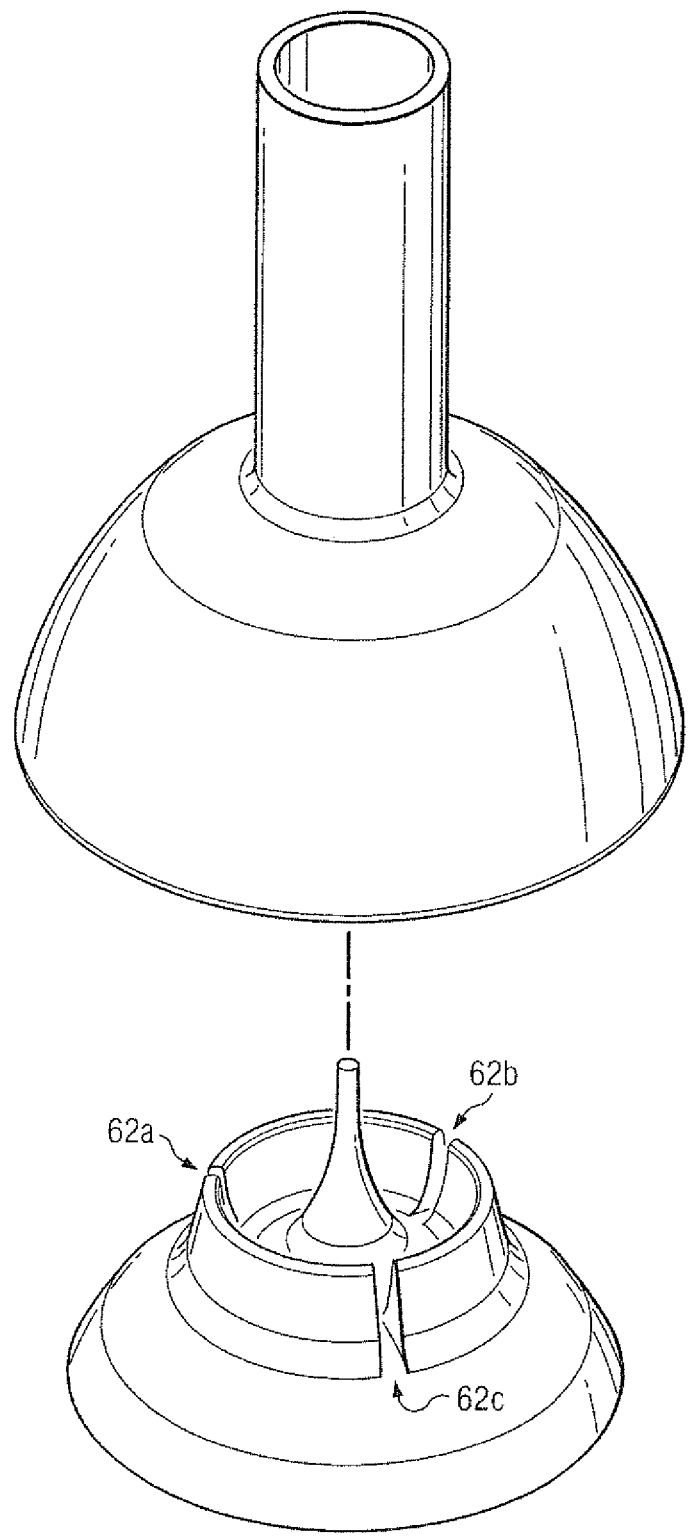

Referring to FIGS. 2A-2C, one embodiment of a non-porous gas delivery mechanism is shown generally at reference numeral 50. Non-porous gas delivery mechanism 50 is configured to successively reflect humidified and/or warmed gas to create a flow of the humidified and/or warmed gas. According to the illustrated embodiment, non-porous gas delivery mechanism includes non-porous surfaces 54 and openings 62.

Non-porous surfaces 74 may include any surface that may reflect humidified and/or warmed gas towards another non-porous surface 74 or towards an open surgical site. For example, according to the illustrated embodiment, the humidified and/or warmed gas may enter non-porous gas delivery mechanism 50 at entry point 52. Once the humidified and/or warmed gas has entered non-porous gas delivery mechanism 50, the humidified and/or warmed gas may be directed towards non-porous surface 54a. Non-porous surface 54a may reflect the humidified and/or warmed gas towards non-porous surface 54b, which may reflect the humidified and/or warmed gas towards the open surgical site, shown generally at reference numeral 60. In the embodiment illustrated in FIG. 2B, non-porous surface 54b illustrates an example of a sidewall of the non-porous gas delivery mechanism 50, and non-porous surface 54a illustrates an example of a non-porous surface oriented such that it is in the path of the gas reflected to or from the sidewall.

Non-porous surfaces 54 may have any size and/or shape. For example, each of the non-porous surfaces 54 may be curved so as to reflect the humidified and/or warmed gas. In particular embodiments, at least a portion of each non-porous surface 54 may have an approximately parabolic shape. In particular embodiments, the approximately parabolic shape may cause the humidified and/or warmed gas to be reflected towards either another non-porous surface 54 or open surgical site 60.

According to the illustrated embodiment, non-porous surface 54a includes a cone shaped portion 56 and a parabolic shaped lip portion 58. The cone shaped portion 56 may be configured to receive the humidified and/or warmed gas and direct the humidified and/or warmed gas to the parabolic shaped lip portion 58. The parabolic shaped lip portion 58 may be configured to reflect the received humidified and/or warmed gas. In particular embodiments, the parabolic shaped lip portion 58 may reflect the humidified and/or warmed gas towards non-porous surface 54b. In particular embodiments, while reflecting the humidified and/or warmed gas towards non-porous surface 54b, a portion of the humidified and/or warmed gas may be reflected towards entry point 52 instead. In particular embodiments, this may further assist in the creation of a smooth, substantially laminar, or laminar flow. Non-porous surface 54b includes a parabolic shaped dome that reflects the humidified and/or warmed gas towards open surgical site 60. In particular embodiments, the shapes of one or more of the portions of non-porous surfaces 54 may not be perfectly parabolic shaped and/or perfectly cone shaped. Instead, due to one or more deviations in the shapes, the shapes of one or more of the portions of non-porous surfaces may be approximately parabolic shaped and/or approximately coned shaped. Although non-porous surfaces 54 have been described as having particular shapes, and portions with particular shapes, non-porous surfaces 54 may have any other shape, or have portions with any other shape, that allows each non-porous surface 54 to reflect the humidified and/or warmed gas towards either another non-porous surface 54 or open surgical site 60.

Non-porous surfaces 54 may be made of any non-porous material type. As is discussed above, a non-porous material may refer to any material that prevents the humidified and/or warmed gas from easily passing through the non-porous material. For example, although the non-porous material may be porous to certain elements, the non-porous material may not be porous to the humidified and/or warmed gas. As such, instead of allowing the humidified and/or warmed gas to pass through the non-porous material, the non-porous material may cause the humidified and/or warmed gas to reflect off the non-porous material. In particular embodiments, the non-porous surfaces 54 may be made of plastic, ceramic, acrylic, or any other material that may be non-porous. In particular embodiments, the non-porous surfaces 54 may be made of medical grade acrylic, such as United States Pharmacopeia (USP) Class VI Medical Grade Acrylic. In particular embodiments the non-porous surfaces 54 may be made of thick thermoform plastic. In particular embodiments, non-porous surfaces 54 may be made of a non-porous material that allows non-porous surfaces 54 to be deformable when pressure is applied to the non-porous surfaces 54.

In particular embodiments, each of the non-porous surfaces 54 within the non-porous gas delivery mechanism 50 may be made of the same material type. In further embodiments, one or more of the non-porous surfaces 54 in the non-porous gas delivery mechanism 50 may be made of different materials. In particular embodiments, the non-porous surface 54 may be made of the same material type as non-porous gas delivery mechanism 50. For example, since non-porous gas delivery mechanism 50 is made up of the non-porous surfaces 54, non-porous gas delivery mechanism 50 may be made of the same non-porous material as the non-porous surfaces 54.

Non-porous surfaces 54 may be made in any manner. For example, each of the non-porous surfaces 54 may be injection molded. In particular embodiments, each non-porous surface 54 may be separately injection molded, and then each non-porous surface 54 may then be coupled together to form non-porous gas delivery mechanism 50. In such embodiments, the non-porous surfaces 54 may be coupled in any manner. For example, the non-porous surfaces 54 may be permanently connected together using any suitable bonding. As another example, the non-porous surfaces 54 may be temporarily coupled together, but may have the ability to be detached from each other. In particular embodiments, all of the non-porous surfaces 54 may be injection molded together as non-porous gas delivery mechanism 50. As such, non-porous surfaces 54 may already be connected together when formed.

According to the illustrated embodiment, non-porous gas delivery mechanism 50 further includes openings 62. Openings 62 may include any element that allows received condensation to drain from non-porous gas delivery mechanism 50. For example, according to the illustrated embodiment, openings 62a-c may be sluice-type reliefs that allow condensation to drain out of non-porous gas delivery mechanism 50. Although FIGS. 2A-2C illustrates openings 62 as sluice-type reliefs, any other element that allows received condensation to drain from non-porous gas delivery mechanism 50 may be used without departing from the scope of the disclosure.

Openings 62 may have any size and/or shape, and may be located at any location on (or in) the non-porous surfaces 54. In particular embodiments, openings 62 may be located on the non-porous surfaces 54 at a location that allows condensation to drain from openings 62. For example, if the shape of a non-porous surface 54 is curved, openings 62 may be located near a lower area of the curve, so that the curvature may cause the condensation to move towards and through the openings 62.

The non-porous surfaces 54 within the non-porous gas delivery mechanism 50 may include any number of openings. For example, the non-porous surfaces 54 may include one opening 62, two openings 62, three openings 62, four openings 62, five openings 62, or any other number of openings 62. Furthermore, each non-porous surface 54 within the non-porous gas delivery system 50 may include a different number of openings 62. For example, while non-porous surface 54a may include three openings 62, non-porous surface 54b may include zero openings 62.

In particular embodiments, openings 62 may prevent condensation from building up in non-porous gas delivery mechanism 50. As such, the condensation may not affect the successive reflections of the humidified and/or warmed gas.

Non-porous gas delivery mechanism 50 may have any size and/or shape. For example, non-porous gas delivery mechanism 50 may have any size that allows non-porous gas delivery mechanism 50 to access (and/or be inserted in) any open surgical site in any patient. As one example of the size of the non-porous gas delivery mechanism 50, non-porous gas delivery mechanism 50 may include the following dimensions:

A=2.125 inches
B=1.748 inches
C=0.500 inch radius
D=1.256 inch radius
E=0.700 inch radius
F=0.103 inches
G=0.350 inches
H=1.000 inches
I=0.582 inches
J=0.045 inches
K=0.044 inches Additionally, although particular dimensions have been described above for non-porous gas delivery mechanism 50, non-porous gas delivery mechanism 50 may have any other size and/or any other dimensions.

Modifications, additions, or omissions may be made to the non-porous gas delivery mechanism 50 without departing from the scope of the invention. The components of the non-porous gas delivery mechanism 50 may be integrated or separated. Moreover, the operations of the non-porous gas delivery mechanism 50 may be performed by more, fewer, or other components. For example, the operations of the two non-porous surfaces 54a-b may be performed by more than two non-porous surfaces 54. As used in this document, "each" refers to each member of a set or each member of a subset of a set.

Figure 2E:
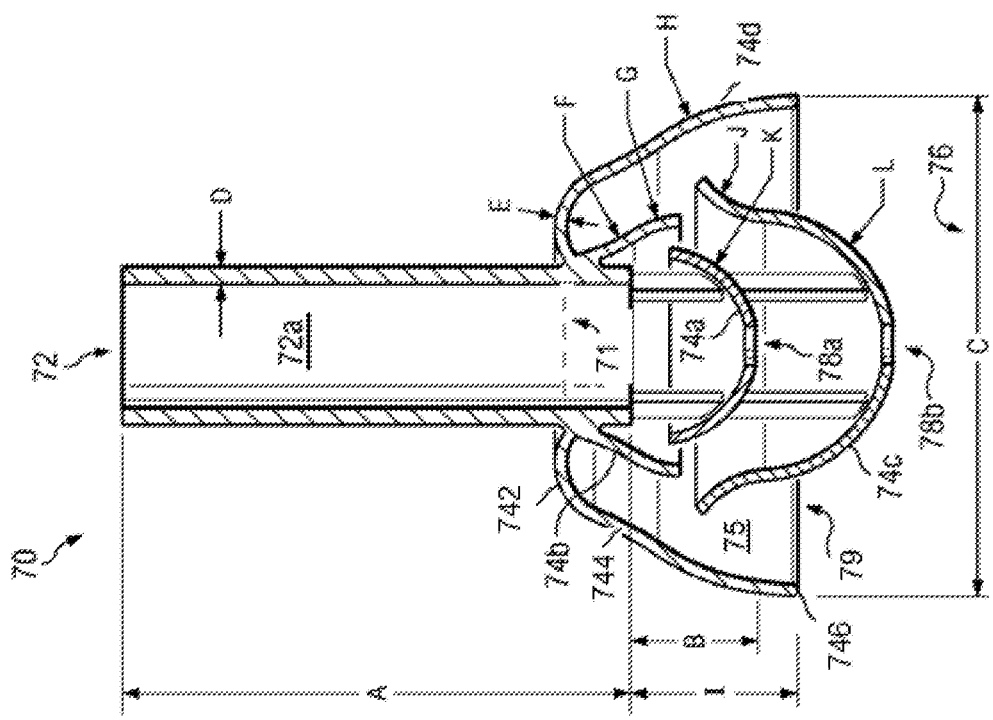
Figure 2D:
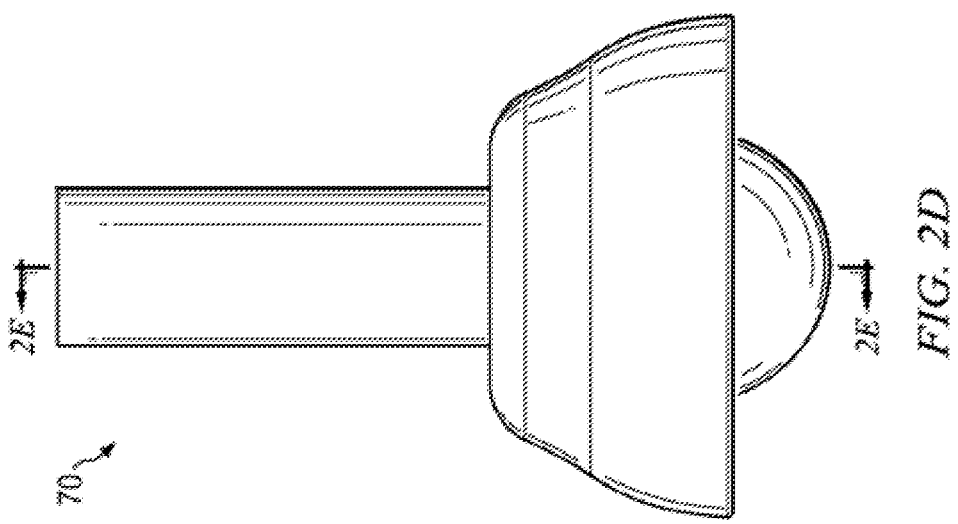

Referring to FIGS. 2D-2E, another embodiment of a non-porous gas delivery mechanism is shown generally at reference numeral 70. Non-porous gas delivery mechanism 70 is configured to successively reflect humidified and/or warmed gas to create a flow of the humidified and/or warmed gas. According to the illustrated embodiment, non-porous gas delivery mechanism includes non-porous surfaces 74 and openings 78.

Non-porous surfaces 78 may include any surface that may reflect humidified and/or warmed gas towards another non-porous surface 78 or towards an open surgical site. For example, according to the illustrated embodiment, the humidified and/or warmed gas may enter non-porous gas delivery mechanism 70 at entry point 72. Once the humidified and/or warmed gas has entered non-porous gas delivery mechanism 70, the humidified and/or warmed gas may be directed towards non-porous surface 74a. Non-porous surface 74a may reflect the humidified and/or warmed gas towards non-porous surface 74b, which may reflect the humidified and/or warmed gas towards non-porous surface 74c. Furthermore, non-porous surface 74c may then reflect the humidified and/or warmed gas towards non-porous surface 74*d*, which may reflect the humidified and/or warmed gas towards the open surgical site, shown generally at reference numeral 76. In the embodiment illustrated in FIG. 2E, non-porous surface 74*d* illustrates an example of a sidewall of the non-porous gas delivery mechanism 70, and non-porous surface 74*a-c* illustrate examples of non-porous surfaces oriented such that they are in the path of the gas reflected to or from the sidewall. In particular embodiments, non-porous surfaces 74 of FIGS. 2D-2E may be similar to non-porous surfaces 54 of FIGS. 2A-2C.

According to the illustrated embodiment, non-porous surface 74*a* includes a parabolic shaped bowl that reflects the humidified and/or warmed gas towards non-porous surface 74*b*. In particular embodiments, while reflecting the humidified and/or warmed gas towards non-porous surface 74*b*, a portion of the humidified and/or warmed gas may be reflected towards entry point 72 instead. In particular embodiments, this may further assist in the creation of a smooth, substantially laminar, or laminar flow. Non-porous surface 74*b* includes a parabolic shaped dome that reflects the humidified and/or warmed gas towards non-porous surface 74*c*. Non-porous surface 74*c* includes a parabolic shaped bowl that reflects the humidified and/or warmed gas towards non-porous surface 74*d*. Non-porous surface 74*d* includes a parabolic shaped dome that reflects the humidified and/or warmed gas towards open surgical site 76. In particular embodiments, the shapes of one or more of the portions of non-porous surfaces 74 may not be perfectly parabolic shaped. Instead, due to one or more deviations in the shapes, the shapes of one or more of the portions of non-porous surfaces may be approximately parabolic shaped. Although non-porous surfaces 74 have been described as having particular shapes, and portions with particular shapes, non-porous surfaces 74 may have any other shape, or have portions with any other shape, that allows each non-porous surface 74 to reflect the humidified and/or warmed gas towards either another non-porous surface 74 or open surgical site 70.

According to the illustrated embodiment, non-porous gas delivery mechanism 70 further includes openings 78. Openings 78 may include any element that allows received condensation to drain from non-porous gas delivery mechanism 70.

For example, according to the illustrated embodiment, openings 78*a* and 78*b* may be drainage openings that allow condensation to drain out of non-porous gas delivery mechanism 70. In particular embodiments, openings 78 may be off-centered. For example, in order to prevent the humidified and/or warmed gas from passing directly through opening 78*a* (e.g., thus allowing the humidified and/or warmed gas to be reflected towards non-porous surface 74*b*), opening 78*a* may not be positioned in the center of non-porous surface 74*a*. Instead, opening 78*a* may be positioned away from the center of non-porous surface 74*a*. In particular embodiments, this may allow condensation to drain from opening 78*a*, but prevent the humidified and/or warmed gas from passing through opening 78*a*. In particular embodiments, opening 78*a* may be positioned in a different location on (or in) non-porous surface 74*a* than opening 78*b* is positioned on non-porous surface 74*c*. As such, condensation that drains from opening 78*a* may not drip directly through opening 78*b*.

The non-porous surfaces 74 within the non-porous gas delivery mechanism 70 may include any number of openings 78. For example, the non-porous surfaces 74 may include one opening 78, two openings 78, three openings 78, four openings 78, five openings 78, or any other number of openings 78. Furthermore, each non-porous surface 74 within the non-porous gas delivery system 70 may include a different number of openings 78. In particular embodiments, openings 78 of FIGS. 2D-2E may be similar to openings 62 of FIGS. 2A-2C.

Non-porous gas delivery mechanism 70 may have any size and/or shape. For example, non-porous gas delivery mechanism 70 may have any size that allows non-porous gas delivery mechanism 70 to access (and/or be inserted in) any open surgical site in any patient. As one example of the size of the non-porous gas delivery mechanism 70, non-porous gas delivery mechanism 70 may include the following dimensions:

A=1.000 inches
B=0.250 inches
C=1.000 inches
D=0.035 inches
E=0.020 inches
F=0.300 inch radius
G=0.185 inch radius
H=0.500 inch radius
I=0.325 inches
J=0.200 inch radius
K=0.200 inch radius
L=0.250 inch radius Additionally, although particular dimensions have been described above for non-porous gas delivery mechanism 70, non-porous gas delivery mechanism 70 may have any other size and/or any other dimensions.

Modifications, additions, or omissions may be made to the non-porous gas delivery mechanism 70 without departing from the scope of the invention. The components of the non-porous gas delivery mechanism 70 may be integrated or separated. Moreover, the operations of the non-porous gas delivery mechanism 70 may be performed by more, fewer, or other components. For example, the operations of the four non-porous surfaces 74*a-d* may be performed by more (or less) than four non-porous surfaces 74.

According to certain embodiments, a surgical method for performing an open surgical site surgery comprises making an incision in a patient, opening the incision in order to create an open surgical site in the patient, receiving a gas from a source, humidifying and warming the gas received from the source, and flowing the humidified and warmed gas through a non-porous gas delivery mechanism, such as non-porous gas delivery mechanism 50 illustrated in FIG. 2B or non-porous gas delivery mechanism 70 illustrated in FIG. 2E.

As an example, FIG. 2B illustrates an embodiment in which non-porous gas delivery mechanism 50 comprises an inlet passage 52*a* connecting to a cup-shaped structure that defines a chamber 55. The cup-shaped structure has a base 542, a rim 546, and a cup-shaped sidewall 544 connecting base 542 to rim 546. Base 542 defines an inlet 51 connecting to inlet passage 52*a* of non-porous gas delivery mechanism 50. Rim 546 defines an outlet 59 positioned opposite the inlet 51. As the humidified and warmed gas flows from inlet 51 to outlet 59, the gas is successively reflected off a plurality of non-porous surfaces within the non-porous gas delivery mechanism 50 to create a flow. At least one of the plurality of non-porous surfaces comprises the cup-shaped sidewall 544. Another of the plurality of non-porous surfaces (such as non-porous surface 54*a*) is positioned within the chamber 55 defined by the cup-shaped structure and oriented such that it is in a path of the gas reflected to or from the cup-shaped sidewall 544 of the non-porous gas delivery mechanism 50.

As another example, FIG. 2E illustrates an embodiment in which non-porous gas delivery mechanism 70 comprises an inlet passage 72a connecting to a cup-shaped structure that defines a chamber 75. The cup-shaped structure has a base 742, a rim 746, and a cup-shaped sidewall 744 connecting base 742 to rim 746. Base 742 defines an inlet 71 connecting to inlet passage 72a of non-porous gas delivery mechanism 70. Rim 746 defines an outlet 79 positioned opposite the inlet 71. As the humidified and warmed gas flows from inlet 71 to outlet 79, the gas is successively reflected off a plurality of non-porous surfaces within the non-porous gas delivery mechanism 70 to create a flow. At least one of the plurality of non-porous surfaces comprises the cup-shaped sidewall 744. Another of the plurality of non-porous surfaces (such as non-porous surface 74a, 74b, or 74c) is positioned within the chamber 75 defined by the cup-shaped structure and oriented such that it is in a path of the gas reflected to or from the cup-shaped sidewall 744 of the non-porous gas delivery mechanism 70.

Figure 3:
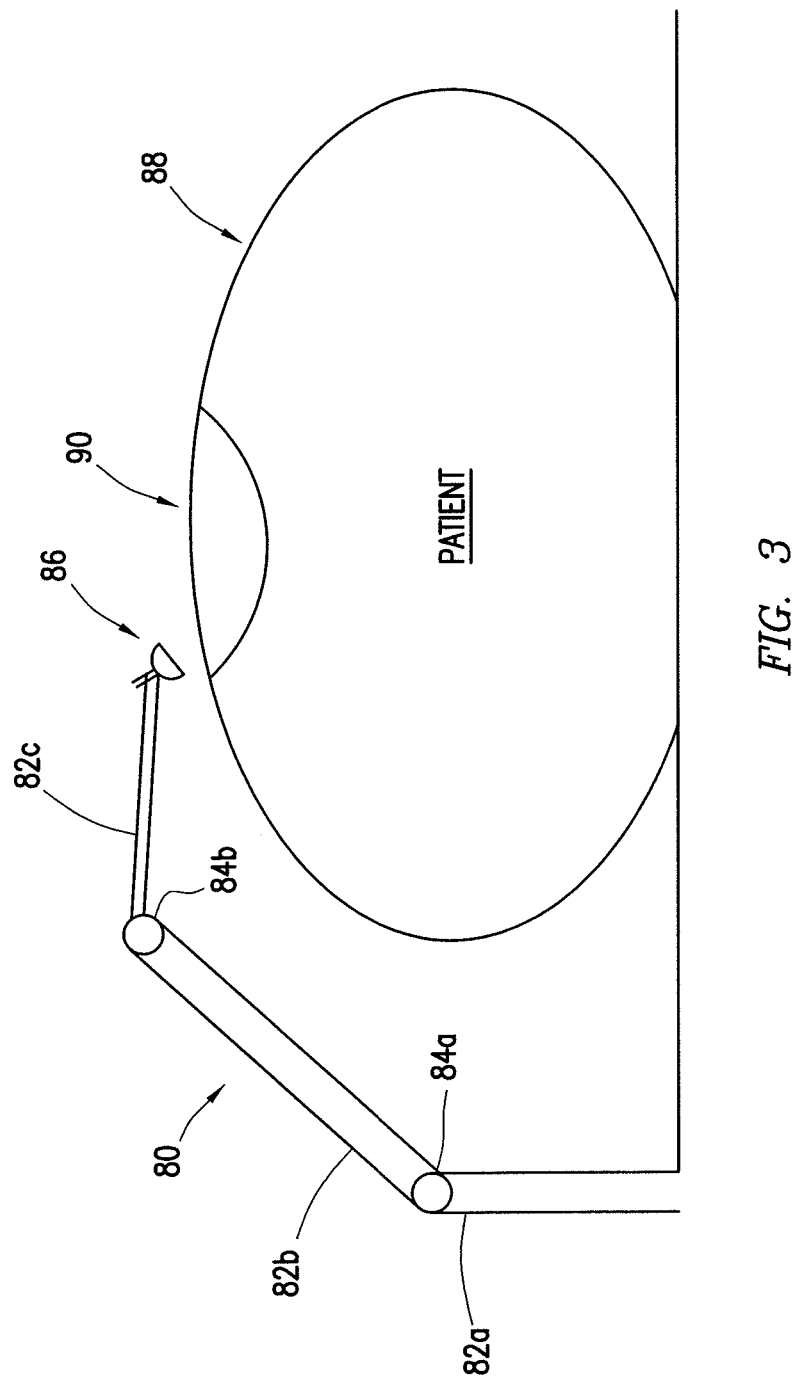
FIG. 3 illustrates an example embodiment of an adjustable arm support that may be used in a surgical method.

Referring to FIG. 3, one embodiment of an adjustable arm support that may be used in a surgical method is shown generally at reference numeral 80. Adjustable arm support 80 is configured to keep a gas delivery mechanism (such as the gas delivery mechanisms described with regard to FIGS. 2A-2C and/or FIGS. 2D-2E, or any other gas delivery mechanism) located outside of the open surgical site during a surgery. In particular embodiments, by keeping the gas delivery mechanism located outside of the open surgical site during a surgery, adjustable arm support 80 may increase the amount of available space inside of the open surgical site. Furthermore, adjustable arm support 80 is further configured to aim (or otherwise position) the gas delivery mechanism so that the gas delivery mechanism provides humidified and/or warmed gas adjacent to or into the open surgical site 90. In particular embodiments, this may allow the gas delivery mechanism 80 to be aimed (or otherwise positioned) without requiring a person (such as a surgeon or other medical staff) to constantly hold and aim the gas delivery mechanism.

According to the illustrated embodiment, adjustable arm support 80 includes arm segments 82, arm joints 84, and coupling mechanism 86. Arm segments 82 may include any type of segment that may allow a gas delivery mechanism to be located outside of the open surgical site 90 of a patient 88 during a surgery. Segments 82 may have any size, shape, and/or material type. For example, segments 82 may have any size that allows a gas delivery mechanism to be positioned above (or otherwise adjacent to) the surgical site 90 of any patient 88. The size of segments 82 may allows a gas delivery mechanism to be positioned above the surgical site 90 of a patient 88 even if the patient is located on an operating table or other apparatus.

According to the illustrated embodiment, adjustable arm support 80 includes three arm segments 82 (e.g., arm segments 82a, 82b, and 82c). Arm segment 82a may be part of the base of adjustable arm support 80. For example, arm segment 82a may be positionable in the floor or permanently coupled to the floor, providing a base for the adjustable arm support 80. As another example, arm segment 82a may include a support base system (not shown) that keeps adjustable arm support upright. In such an example, the support base system may include wheels (or any other mobility enhancing mechanisms) that may be used to move the adjustable arm support 80. The wheels (or other mobility enhancing mechanisms) may include a locking device that prevents the wheels (or other mobility enhancing mechanisms) from being used to move the adjustable arm support 80 when the locking device is engaged. As a further example, arm segment 82a may be coupled to (or capable of being coupled to) a wall, ceiling, or any other surface. As such, adjustable arm support 80 may not use up (or may use up very little) floor space in an operating room. Arm segments 82b and 82c may provide adjustable arm support 80 with further size, reach, and adjustment capabilities. For example, arm segments 82b and 82c may allow adjustable arm support 80 to position a gas delivery mechanism outside of the open surgical site 90 while still allowing the humidified and/or warmed gas to be delivered adjacent to or into the open surgical site 90. Although FIG. 3 illustrates adjustable arm support 80 as including three arm segments 82, adjustable arm support 80 may include any other number of arm segments 82. For example, adjustable arm support 80 may include more than three arm segments 82 or less than three arm segments 82.

Arm joints 84 may include any type of coupling device that couples arm segments 82 together and that allows the position of the arm segments 82 to be adjusted in relation to each other. For example, arm joints 84 may be spherical-type joints that allow an arm segment 82 to be adjusted in any direction. As another example, arm joints 84 may be revolute-type joints that allow an arm segment 82 to be adjusted in particular directions. Arm joints 84 may allow the arm segments 82 of adjustable arm support 80 to be adjusted so that adjustable arm support 80 may position a gas delivery mechanism above (or otherwise adjacent to) the surgical site 90.

According to the illustrated embodiment, adjustable arm support 80 includes two arm joints 84 (arm joints 84a and 84b). Arm joint 84a couples arm segment 82b to arm segment 82a, and allows the position of arm segment 82b to be adjusted in relation to arm segment 82a. Arm joint 84b couples arm segment 82c to arm segment 82b, and allows the position of arm segment 82c to be adjusted in relation to arm segment 82b. Although FIG. 3 illustrates adjustable arm support 80 as including two arm joints 84, adjustable arm support 80 may include any other number of arm joints 84. For example, adjustable arm support 80 may include more than two arm joints 84 or less than two arm joints 84.

Coupling mechanism 86 may include any mechanism that couples a gas delivery mechanism (such as the gas delivery mechanisms described with regard to FIGS. 2A-2C and/or FIGS. 2D-2E, or any other gas delivery mechanism) to adjustable arm support 80. For example, coupling mechanism 86 may include a clamping device, a cupping device that holds a gas delivery mechanism, or any other mechanism that may couple a gas delivery mechanism to adjustable arm support 80. Coupling mechanism 86 may be capable of aiming (or otherwise positioning) the gas delivery mechanism so that the gas delivery mechanism provides humidified and/or warmed gas adjacent to or into the open surgical site 90. Coupling mechanism 86 may aim (or otherwise position) the gas delivery mechanism in any direction. In particular embodiments, coupling mechanism 86 may be capable of aiming (or otherwise positioning) the gas delivery mechanism independent of any other components of the adjustable arm support 80. In particular embodiments, coupling mechanism 86 (in conjunction with one or more other components of adjustable arm support 80) may be capable of aiming (or otherwise positioning) the gas delivery mechanism.

Coupling mechanism 86 may aim (or otherwise position) the gas delivery mechanism for any amount of time. For example, the coupling mechanism 86 may aim (or otherwise position) the gas delivery mechanism for the entire time that the surgery uses humidified and/or warmed gas. As another example, the coupling mechanism 86 may aim (or otherwise position) the gas delivery mechanism for only portions of the surgery. In particular, the gas delivery mechanism may be uncoupled from the coupling mechanism 86 during the surgery in order to be placed into the surgical site 90 (or any other location) for a period of time. This may allow the gas delivery mechanism to be located outside of the surgical site 90 for portions of the surgery, and may further allow the gas delivery mechanism to be located inside of the surgical site 90 for other portions of the surgery (such as if humidified and/or warmed gas needs to be provided inside the surgical site 90 for portions of the surgery). Coupling mechanism 86 may include a locking device that may prevent the gas delivery mechanism from being moved, adjusted, or accidentally re-positioned (such as if it was bumped by a person) while the locking device is engaged.

Modifications, additions, or omissions may be made to the adjustable arm support 80 without departing from the scope of the invention. The components of the adjustable arm support 80 may be integrated or separated. Moreover, the operations of the adjustable arm support 80 may be performed by more, fewer, or other components.

Figure 4:
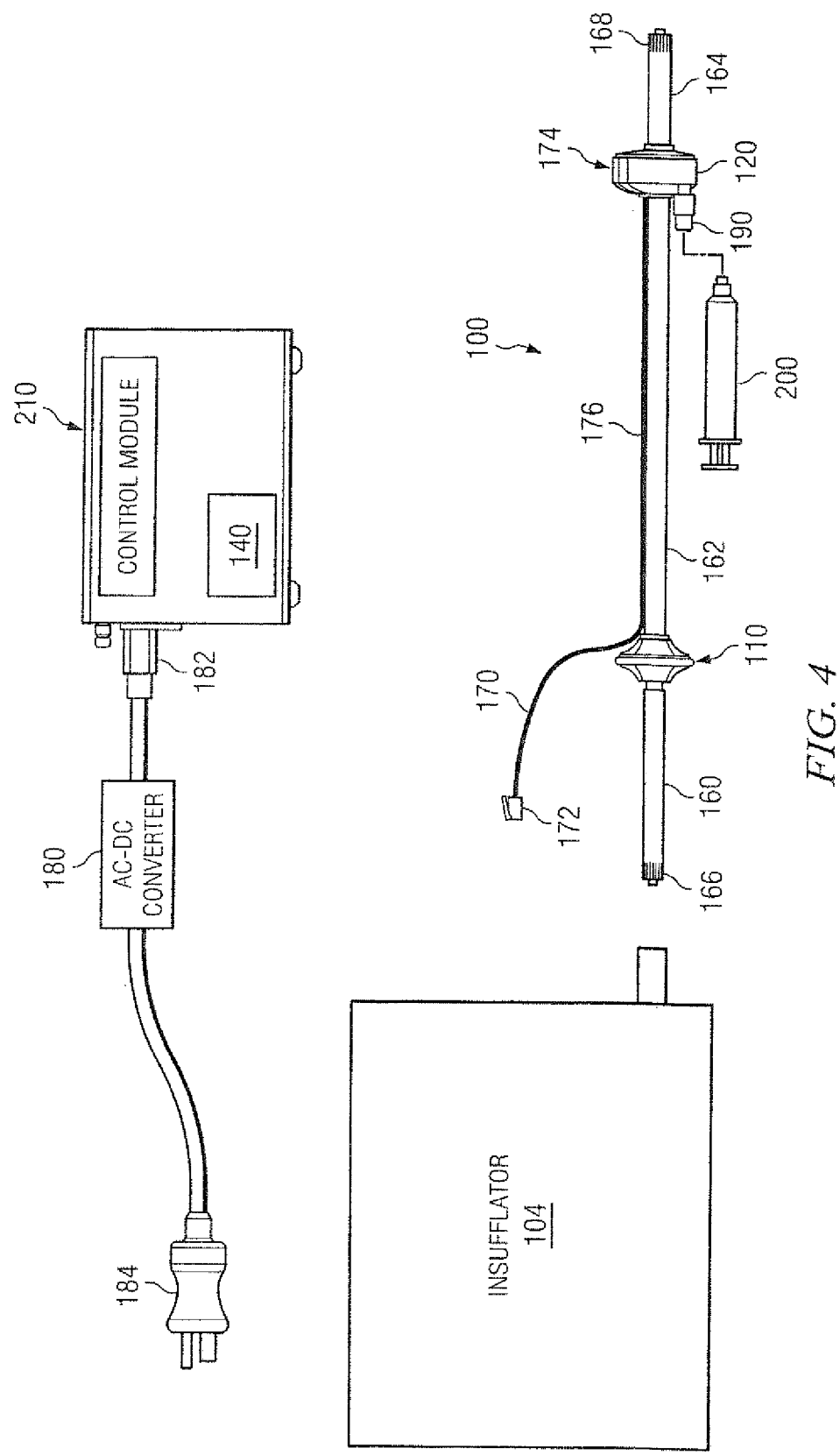
FIG. 4 is a schematic view of one embodiment of an apparatus that may be used in a surgical method.

Referring to FIG. 4, one embodiment of an apparatus for treating or conditioning insufflation gas is shown generally at reference numeral 100. The apparatus 100 is adapted to receive gas from a gas source (high or low pressure, high or low flow rate), such as insufflation gas from an insufflator 104 for delivery adjacent to or into an open surgical site. The apparatus comprises a filter 110, a heater/humidifier 120, and a control module 140. A tubing set (or conduit set) is provided to connect the various components of the apparatus together. Specifically, a first tube segment 160 connects the outlet of the insufflator 104 to the inlet tubing of the filter 110 via a male Luer lock 166 or any appropriate adapter compatible with the insufflator outlet port. A second tube segment 162 connects the outlet of the filter 110 to the inlet of the heater/humidifier 120. A third tube segment 164 connects the outlet of the heater/humidifier 120 by a male Luer lock 168 (or other appropriate fitting adapter) to a gas delivery device (not shown), such as the non-porous gas delivery mechanisms described with regard to FIGS. 2A-2C and/or FIGS. 2D-2E, or any other non-porous gas delivery mechanism that successively reflects the humidified and/or warmed gas. The tubing of the tube segments 160, 162 and 164 may be flexible and sufficiently long to permit the insufflator 104 and control module 140 to be placed at a convenient distance from a patient, while the heater/humidifier 120 may be placed within 12 inches of the patient.

The filter 110 is optional, but may be a particulate filter (for example a BF201 filter from AG Industries, with a HA-8141 filter media from Hollingsworth & Vose) having a pore size preferably small enough to exclude all solid particles and bacterial or fungal agents that may have been generated in a gas supply cylinder, such as a carbon dioxide cartridge, or the insufflator 104 (e.g., 0.5 micron or less, for example, about 0.3 micron). As another example, the filter 110 may be a DDF5500M02C-LM particulate filter from Porous Media. As a further example, the filter 116 may be a HWB-FLTR-CO2-1 particulate filter from AG Industries. In one embodiment, the filter 110 is a hydrophobic filter. In another embodiment, the filter 110 is a hydrophilic filter. In a further embodiment, decreasing the pore size of filter 110 below 0.3 micron may cause a concomitant increase in pressure drop of gas, and thus flow rate may be reduced significantly. In one embodiment, the filter 110 may be disposed in the apparatus 100 in any suitable location. For example, the filter 110 may be disposed in the apparatus 100 in a location where the gas passes through the filter 110 before entering the heater/humidifier 120. As such, the gas may be filtered prior to being humidified and warmed. In another embodiment, the filter 110 may be disposed in the apparatus 100 in a location where the gas enters the filter 110 after exiting the heater/humidifier 120. As such, the gas may be filtered after being humidified and warmed.

In one embodiment, the heater/humidifier 120 is connected by tubing to a gas delivery device, such as a surgical instrument, so that the gas travels a short distance from the outlet of the heater/humidifier 120 to the conduit or connection to the interior of a patient. The purpose of this arrangement may be to allow gas to be delivered to the patient while still at a temperature and water content sufficiently close to the physiological interior body temperature and humidity. That is, the apparatus according to the disclosure may reduce thermodynamic cooling of medical gases in transit to the patient, because it provides a highly efficient humidifying and warming chamber that, as a result of its efficiency, can be quite compact and thus be positioned very near to the patient.

In one embodiment, the control module 140 is contained within an electrical housing 210 and is connected to the heater/humidifier 120 by several wire pairs contained within an insulated electrical cable 170. In particular, the cable 170 has a connector 172 at one end that electrically connects into a receptacle of the housing 210 for the control module 140, and at the other end it is electrically connected to the heater/humidifier 120 by a sealed electrical feedthrough 174. In one embodiment, the cable 170 is attached to the tube segment 162 by a plastic tape or clip 176. In another embodiment, the cable 170 is attached to the tube segment 162 by heat seal, extrusion, ultrasonic welding, laser transmission welding, glue or is passed through the interior of tube segment 162.

The control module 140 and associated components in the heater/humidifier 120 may be powered by an AC-DC converter 180. In one embodiment, the AC-DC converter 180 has an output that is connected by a plug connector 182 into a receptacle of the housing 210 to the control module 140, and has a standard AC wall outlet plug 184 that can be plugged into standard AC power outlets. For example, the AC-DC converter 180 is plugged into an AC power strip that is provided on other equipment in an operating room. In another embodiment, electrical power for the apparatus is provided by a battery or photovoltaic source. In further embodiments, circuitry may be provided in the control module 140 that operates on AC signals, as opposed to DC signals, in which case the control module 140 could be powered directly by an AC outlet.

In one embodiment, the heater/humidifier 120 has a charging port 190 that is capable of receiving a supply of liquid therethrough to charge the humidification means (described hereinafter) with liquid. For example, a syringe 200 containing a predetermined volume of liquid is introduced into the charging port 190 to inject liquid into the heater/humidifier 120 for an initial charge or re-charge of liquid. The apparatus 100 may be sold with the heater/humidifier 120 pre-charged with a supply of liquid such that an initial charge is not required for operation.

Modifications, additions, or omissions may be made to the apparatus 100 without departing from the scope of the invention. The components of the apparatus 100 may be integrated or separated. Moreover, the operations of the apparatus 100 may be performed by more, fewer, or other components. For example, the operations of the heater/humidifier 120 may be performed by more than one component.

Figure 5:
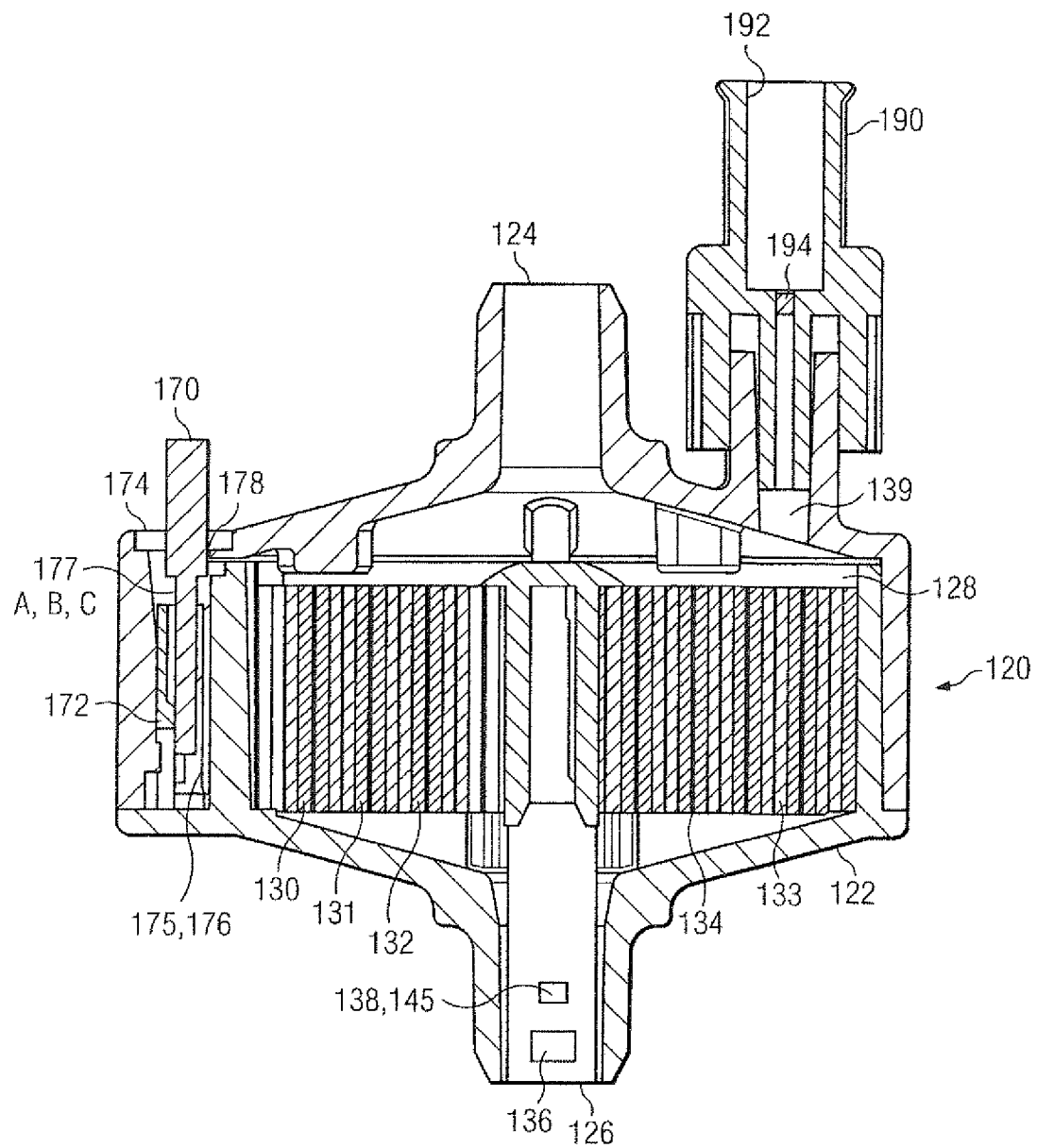
FIG. 5 is a cross-sectional view of one embodiment of a heater/humidifier of an apparatus that may be used in a surgical method.

Turning to FIG. 5, one embodiment of the heater/humidifier 120 will be described in greater detail. In this embodiment, the heater/humidifier 120 comprises a housing 122 having an (entry port) inlet 124 and an (exit port) outlet 126. The housing 122 defines a chamber 128 that contains elements for substantially simultaneously humidifying (hydrating) and warming the gas supplied through the inlet 124, as well as means for sensing the temperature of the gas and the relative humidity of the gas as it exits the chamber 128.

In this embodiment, within the chamber 128, there is provided a humidification means that may be comprised of one or more layers of liquid-retaining or absorbing padding or sponge material, shown at reference numerals 130, 131 and 132. It should be understood that the number, spacing and absorbency of the liquid-retaining layers 130, 131 and 132 may be varied according to specific applications. Three liquid-retaining layers are shown as an example. The material of the liquid-retaining layers 130, 131 and 132 can be any desirable liquid-retaining material, such as a hydrophylic material (e.g., Knowlton 1430 by Hydration media). The pore size of the selected material may be chosen according to a balance of water retention capabilities and low pressure drop considerations. The larger the pore size, the greater the water retention capability for humidification.

In particular embodiments, the humidification means may consist of a chamber of liquid (without liquid-retaining layers) having one or more semi-permeable membranes on opposite ends to allow gas to pass therethrough. The liquid in the chamber could be warmed by a heating jacket placed around the chamber to thereby humidify and warm the gas passed therethrough. In another embodiment, the humidification means may be disposed in any suitable location and in any suitable manner in the chamber. For example, the humidification means may be disposed in the chamber so that gas flows through the humidification means and/or flows over, under, and/or around the humidification means. In a further embodiment, the chamber may include a further humidification means that is separate from the humidification means. For example, the chamber may further include a humidification chamber that may aerosolize a liquid, such as an anesthetic discussed above in FIG. 1, into the gas. In such an example, the humidification chamber may include any suitable amount of the liquid, such as 2 cc. In a further embodiment, the humidification means may include any suitable amount of the liquid, such as 0.1 cc-15 cc. In one embodiment, the amount of the liquid included in the humidification means may be determined based on the dimensions of the humidification means and/or the holding capacity of any material in the humidification means.

In one embodiment, the heating means in the heater/humidifier 120 comprises at least one heating element 134 positioned in the housing (substantially) co-located with the humidification means, such as between the liquid-retaining layers 130 and 131. The heating element 134 may be an electrically resistive wire, for example, and is described in more detail hereinafter in conjunction with FIG. 6. The heating element 134 may be positioned within the humidification means insofar as it is placed preferably between liquid-retaining layers. The heating element 134 warms the insufflation gas supplied through the inlet, under control of a heat control signal supplied by the control module 140, substantially simultaneously with the humidification of the gas as the gas passes through the chamber 128. Additional heating elements may be disposed within the chamber.

Other types of heating elements may be used without departing from the scope of the invention. The heating elements may be placed anywhere in the chamber. In some embodiments, multiple chambers may be used to serially humidify and warm the gas, or serial chambers could both humidify and warm or apply a pharmacologic agent.

According to one embodiment, in order to sense the temperature and humidity of the gas as it exits the heater/humidifier 120, a temperature sensor 136 and a relative humidity sensor 138 may be provided. In one embodiment, the temperature sensor 136 may be provided anywhere within the flow of gas. In a further embodiment, the temperature sensor 136 may be provided in any other location that allows it to sense the temperature of the gas. In one embodiment, the temperature sensor 136 is a thermistor. In one embodiment, the temperature sensor 136 may be accurate to within about 0.2° C. In particular embodiments, the temperature of the gas may be sensed after the gas has been humidified so that any change in the temperature of the gas as it is humidified is corrected at that point in the apparatus, thereby compensating for enthalpy changes. In an alternative embodiment, temperature of the gas can be sensed indirectly by sensing the temperature of the heater. Infrared sensors could also be used.

In one embodiment, the humidity sensor 138 is positioned in the flow path of gas exiting the chamber 128, preferably downstream from the heating element 134 either between liquid-retaining layers or on the downstream side of the liquid-retaining layers, proximate the exit port 126 of the housing 122. Humidity sensor 138 is optional as is a temperature sensor. The humidity sensor 138 is preferably not in contact with a liquid-retaining layer. FIG. 5 shows the humidity sensor 138 distal to the liquid-retaining layers, separated from the liquid-retaining layer 132 by a porous mesh (plastic or metal) layer 133 that extends across the interior of the housing 122. The humidity sensor 138 actually is generally not in contact with the porous mesh layer 133, but is spaced therefrom as well. The humidity sensor 138 may be a humidity-sensitive capacitor sensor, such as a capacitive humidity sensor manufactured by Philips Corporation, which changes capacitance in response to humidity changes. Other humidity sensors can also be used. The humidity sensor 138 measures the relative humidity of the gas as it passes through the chamber 128 to enable monitoring of the gas humidity, and in order to provide an indication of the amount of liquid remaining in the humidification means, e.g., in liquid-retainer layers 130, 131 and 132. As will be explained hereinafter, a timer/divider integrated circuit (IC) 145 (FIG. 8), is connected to the humidity sensor 138 and may be disposed within the housing 122 together and substantially co-located with the humidity sensor 138.

According to one embodiment, electrical connections to the components inside the housing 122 of the heater/humidifier 120 are as follows. A ground or reference lead (not specifically shown) is provided that is connected to each of the temperature sensor 136, heating element 134 and humidity sensor 138-timer/divider 145. A wire 175 (for a positive lead) electrically connects to the heating element 134 and a wire 176 (for a positive lead) electrically connects to the temperature sensor 136. In addition, three wires 177A, 177B and 177C (shown in more detail in FIG. 8) electrically connect to the humidity sensor 138-timer divider circuitry, wherein wire 177A carries a DC voltage to the timer/divider 145, wire 177B carries an enable signal to the timer/divider 145, and wire 177C carries an output signal (data) from the timer/divider 145. All of the wires are fed from the insulated cable 170 into the feedthrough 174 and through small holes in the housing 122 into the chamber 128. The feedthrough 174 is sealed at the opening 178 around the cable 170. The optional charging port 190 is attached to a lateral extension 139 of the housing 122. The charging port 190 comprises a cylindrical body 192 containing a resealable member 194. The resealable member 194 permits a device to be inserted therethrough, but seals around the exterior of the device. This allows a volume of liquid (sterile water, saline, etc.) to be delivered into the chamber 128 without releasing the liquid already contained therein. The resealable member 194 is, for example, a Luer lock check valve, such as P/N B900-SSM41 manufactured by NP Medical or P/N SCV23050 manufactured by Value Plastics. Alternatively, the charging port may be embodied by a one-way valve, a sealable port, a screw cap, a cap with a slit to permit the introduction of a syringe or other device, such as a SAFE-LINE injection site, part number NF9100, manufactured by B. Braun Medical Inc., or any other covering material or member capable of permitting the introduction of a device and preventing the backflow of contained liquid or gas. In one embodiment, the chamber 128 may contain approximately 3 to 8 cubic centimeters (cc) (but possibly as much as 10 cc) of liquid, and it may be desirable that the gas have a dwell time within the chamber of at least approximately 0.01 to 1.0 sec. A liquid volume of 8 cc in the chamber 128 will usually be adequate for conditioning approximately 180 liters of insufflation gas at a relative humidity of 80-95%. The control module 140, however, may issue a warning when the humidity of the gas being treated by the heater/humidifier 120 drops below a predetermined relative humidity, as explained hereinafter. Charging ports may be included for recharging or charging of a pharmacologic agent (such as an anesthetic or antibiotic).

In one embodiment, the housing 122 may have a length to width ratio of about 1:2 to about 1:10. In a further embodiment, the housing 122 may have a length to width ratio of about 1:3 to about 1:4. In one embodiment, the length of the housing 122 may be from about 0.5 cm to about 1.5 cm, and the diameter may be about 3.0 cm to about 5.0 cm. For example, one embodiment of the housing 122 is approximately 3.5 centimeters (cm) in diameter and 1.0 cm thick. The length and width of chamber 128 can be varied such that proper humidification and warming occur. In one embodiment, an elongated housing configuration would permit the heater/humidifier 120 to be less intrusive to the medical attendant or surgeon and also be freely movable with respect to other equipment in or around the apparatus 100. Any length to width ratio may be used without departing from the scope of the invention.

In one embodiment, the desirable width and diameter of the chamber may also be dependent upon the rate of gas flow from insufflator 104, which is usually from about 1-20 liters/minute, and upon the pressure desired to be maintained, which is affected more by the diameter of chamber 128 than by its length. A person of ordinary skill in the art, given the teachings and examples herein, can readily determine suitable dimensions for chamber 128 without undue experimentation.

Modifications, additions, or omissions may be made to the heater/humidifier 120 without departing from the scope of the invention. The components of the heater/humidifier 120 may be integrated or separated. Moreover, the operations of the heater/humidifier 120 may be performed by more, fewer, or other components. For example, the operations of the heating element 134 may be performed by more than one component.

Figure 6:
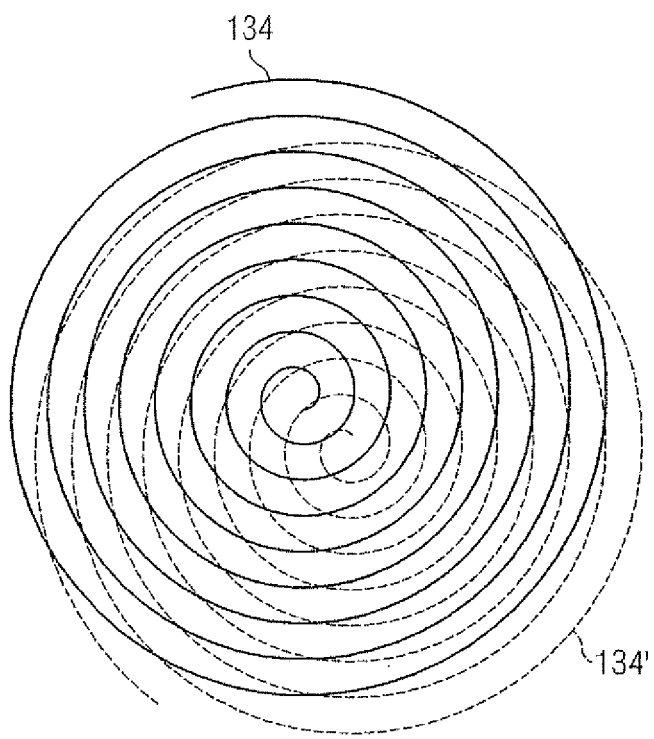
FIG. 6 is a schematic diagram of one embodiment of a heating element of an apparatus that may be used in a surgical method.

Referring to FIG. 6, one embodiment of the heating element 134 is shown in more detail. The heating element 134 is an electrically resistive wire that is disposed in the housing 128 in a concentrical coil configuration having a predetermined number of turns, such as 6-8 turns. In another embodiment, a second heating element 134' is provided that is arranged with respect to the heating element 134 such that its coils are offset from those of the first heating element, relative to the direction of gas flow through the chamber. In one embodiment, if two or more heating elements are employed, they are preferably spaced from each other in the chamber of the heater/humidifier by approximately 3-4 mm. The first and second heating elements 134 and 134' can be coiled in opposite directions relative to each other. This arrangement allows for maximum contact of the gas flowing through the chamber with a heating element. Other non-coiled configurations of the heating element 134 are also suitable.

Modifications, additions, or omissions may be made to the heating element 134 without departing from the scope of the invention. The components of the heating element 134 may be integrated or separated. Moreover, the operations of the heating element 134 may be performed by more, fewer, or other components.

Figure 7:
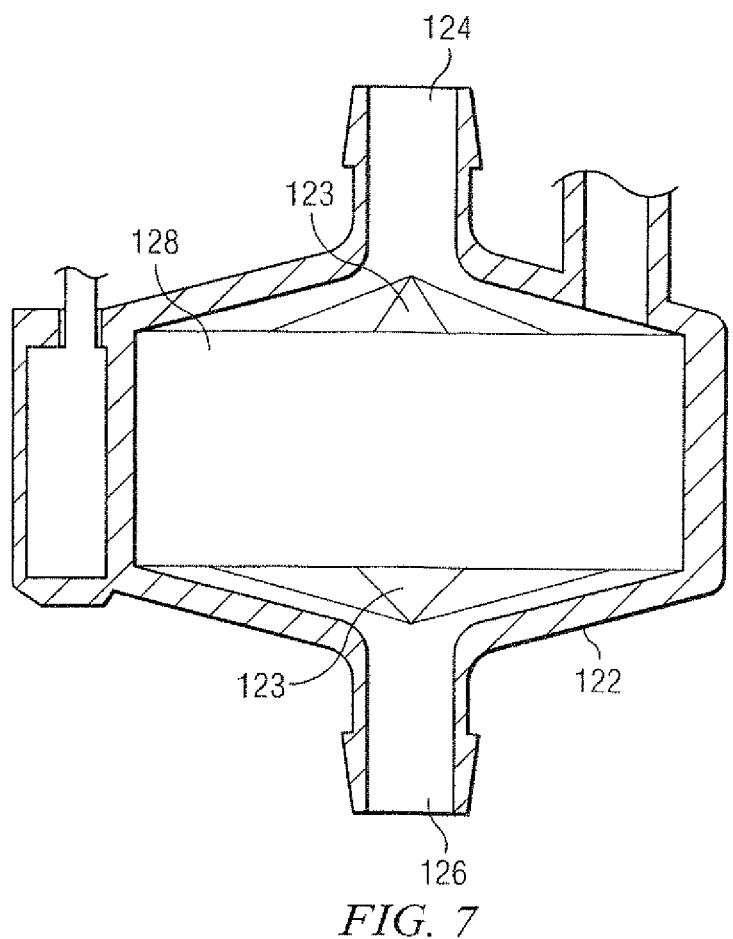
FIG. 7 is a cross-sectional view of one embodiment of a heater/humidifier of an apparatus that may be used in a surgical method.

Turning to FIG. 7, another feature of one embodiment of the heater/humidifier 120 is illustrated. At the inlet and/or outlet of the housing 122, fluted surfaces 123 may be provided to facilitate complete dispersion of gas as it is supplied to the heater/humidifier 120. This improves the fluid dynamics of the gas flow through the chamber 128 to ensure that the gas is uniformly humidified and warmed as it flows through the chamber 128.

Figure 8:
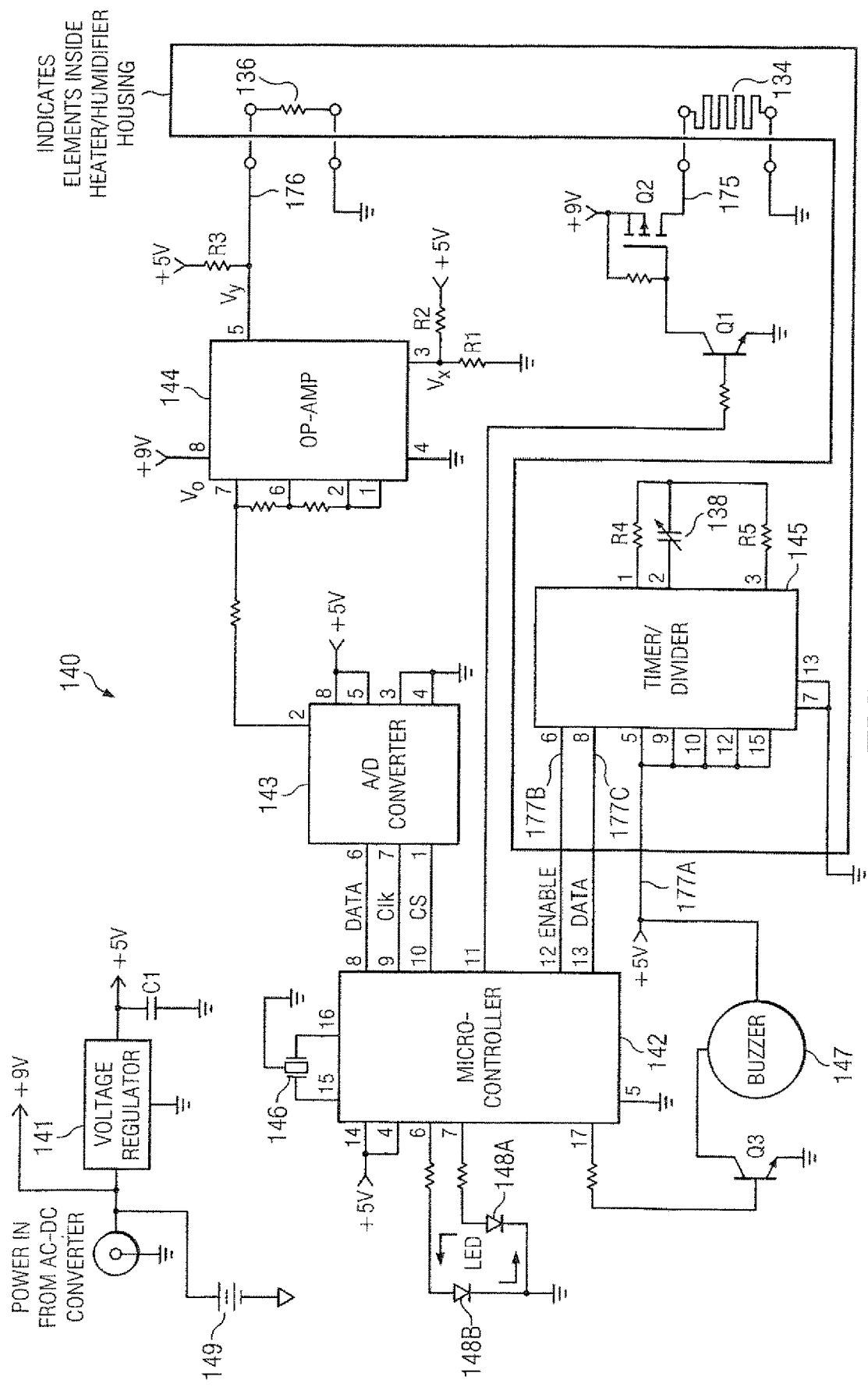
FIG. 8 is a schematic diagram showing one embodiment of a control circuit of an apparatus that may be used in a surgical method.

Referring to FIG. 8, one embodiment of the control module 140 will be described in detail. The control module 140 contains an example of monitoring circuitry and an example of control circuitry for the apparatus 100, and comprises a voltage regulator 141, a microcontroller 142, an A/D converter 143, a dual operational amplifier (hereinafter "op-amp") module 144, and a timer/divider 145. The monitoring circuit portion of the control module 140 comprises the combination of the microcontroller 142 and timer/divider 145. The control circuit portion of the control module 140 consists of the microcontroller 142, A/D converter 143 and op-amp module 144. The monitoring circuit monitors the relative humidity of gas exiting the chamber based on a signal generated by the timer/divider 145. The control circuit monitors the temperature of the gas exiting the chamber and in response, controls electrical power to the heating element to regulate the temperature of the gas to a temperature within a range of temperatures. In one embodiment, while the temperature of the gas exiting the chamber is actively controlled, the relative humidity of the gas in the chamber may not be actively controlled. For example, in one embodiment, the relative humidity of the gas may be monitored and an alert may be generated when it drops below a predetermined threshold so that appropriate action can be taken, such as replenishing the heater/humidifier with liquid.

FIG. 8 shows that, in one embodiment, several components may be located within the electrical housing 210 (FIG. 4), whereas other components may be located within the housing of the heater/humidifier 120 (FIG. 5). In particular, the timer/divider 145 and the associated resistors R4 and R5 may be located inside the housing 122 of the heater/humidifier 120, together with the humidity sensor 138 in a circuit package that includes the humidity sensor 138 exposed on one or more surfaces thereof. More specifically, the timer/divider 145 is co-located with humidity sensor 138. This configuration minimizes timing error by stray wiring inductance and capacitance (sensor kept close to active circuits of timer/divider 145). In addition, by co-locating the timer/divider 145 and humidity sensor 138, the need for interconnecting wires is eliminated, thereby avoiding undesirable signal radiation. However, any location arrangement of components is allowable.

The voltage regulator 141 receives as input the DC output of the AC-DC converter 180 (FIG. 4), such as for example, 9 V DC, that is suitable for use by the analog components of the control module. The voltage regulator 141 regulates this voltage to generate a lower voltage, such as 5 V DC, for use by the digital components of the control module. The capacitor C1 at the output of the voltage regulator 141 serves to filter out any AC components, as well known in the art. Alternatively, a suitable DC voltage is provided by a battery or photovoltaic source shown at reference numeral 149.

In one embodiment, the microcontroller 142 is a PIC16C84 integrated circuit microcontroller that controls system operation. A ceramic resonator 146 (4 MHz) is provided to supply a raw clock signal to pins 15 and 16 of the microcontroller 142, which uses it to generate a clock signal for the signal processing functions explained hereinafter.

The op-amp 144 module may be coupled (by wire 176) to the temperature sensor 136 (thermistor). The op-amp module 144 is, for example, a LTC1013 dual low-input-offset-voltage operational amplifier integrated circuit that includes two op-amps, referred to hereinafter as op-amp A and op-amp B. The non-inverting input of the op-amp A of the op amp module 144 is pin 3, and pin 2 is the inverting input. The output of op-amp A is pin 1. Op-amp A of the op-amp module 144 is used to buffer the output voltage of the voltage divider formed by resistors R1 and R2. The buffered output voltage, referred to as Vx in FIG. 8, is applied to op-amp B in the op-amp module 144. Op-amp B is configured as a non-inverting-with-offset amplifier with a gain of 21.5, and also receives as input the output of the temperature sensor 136, adjusted by resistor R3, shown as voltage Vy in the diagram. The output voltage of op-amp B is at pin 7, referred to as Vo in FIG. 8. The output voltage Vo is equal to 21.5 Vy−20.5 Vx, which is inversely proportional to the gas temperature in the housing of the heater/humidifier. The output voltage Vo ranges between 0-5 V DC, depending on the temperature of the gas in the chamber.

In one embodiment, the A/D converter 143 is an ADC 0831 integrated circuit analog-to-digital converter that receives as input at pin 2, the output Vo of the op-amp module 144. The A/D converter 143 generates a multi-bit digital word, consisting of 8 bits for example, that represents the output voltage Vo, and is supplied as output at pin 6, which in turn is coupled to I/O pin 8 of the microcontroller 142. The microcontroller 142 commands the A/D converter 143 to output the digital word by issuing a control signal on I/O pin 10 which is coupled to the chip select pin 1 of the A/D converter 143. Moreover, the microcontroller 142 controls the rate at which the A/D converter 143 outputs the digital word by supplying a sequence of pulses on pin 9 applied to clock input pin 7 of the A/D converter 143. The "unbalanced bridge" values of resistors R1, R2 and R3 may be chosen to produce a 0-5 V DC output over gas temperatures from approximately 20° C. to approximately 45° C. Since the bridge and the reference for the A/D converter 143 are provided by the same 5 V DC source, error due to any reference voltage shift may be eliminated.

The timer/divider 145 is, for example, a MC14541 precision timer/divider integrated circuit. The humidity sensor 138 is connected to pin 2 and to resistors R4 and R5 as shown. In response to an enable signal output by the microcontroller 142 on pin 12 that is coupled to timer/divider pin 6, the timer/divider 145 generates an output signal that oscillates at a rate determined by the value of the resistor R4, the capacitance of the humidity sensor 138 (which varies according to the relative humidity of the gas inside the heater/humidifier housing) and a predetermined divider constant. For example, the divider constant is 256. Specifically, the output signal of the timer/divider 145 is a square wave oscillating between 0 V ("low") and 5 V ("high") at a frequency of approximately $1/[256*2.3*R4_t*C_t]$Hz, where $R4_t$ is, for example, 56 kOhms, and $C_t$ is the capacitance at some time (t) of the relative humidity sensor 138 depending on the relative humidity of the gas in the chamber. For example, the humidity sensor manufactured by Phillips Electronics, referred to above, can measure between 10-90% RH (relative humidity), where $C_t$ at 43% RH is 122 pF (+/−15%), with a sensitivity of 0.4+/−0.5 pF per 1% RH. The output signal of the timer/divider 145 appears at pin 8, which is coupled to the I/O pin 13 of the microcontroller 142. Thus, the timer/divider 145 may essentially be an oscillator circuit connected to the humidity sensor that generates an output signal with a frequency dependent on a capacitance of the humidity sensor. In one embodiment, any oscillator circuit that can generate as output a signal whose frequency is dependent on a variable capacitance may be suitable for the timer/divider 145.

In one embodiment, the microcontroller 142 computes a measure of the relative humidity of the gas inside the heater/humidifier housing by timing or measuring a characteristic of the output signal of the timer/divider 145. For example, the microcontroller 142 measures the time duration of one of the phases of the output signal of the timer/divider 142, such as the "high" phase which is approximately $\frac{1}{2}*[256*2.3*R4_t*C_t]$. This time duration may be indicative of the relative humidity of the gas in the chamber of the heater/humidifier since the rate of the oscillation of the timer/divider depends on the capacitance of the humidity sensor 138, as explained above. For example, for a change in RH of 10-50% and/or 50 to 90%, there is a 13% change in the duration of the "high" phase of the timer/divider output signal. The microcontroller 142 monitors the relative humidity of the gas exiting the chamber in this manner and when it drops below a predetermined relative humidity threshold (indicated by a corresponding predetermined change in the oscillation rate of the timer/divider 145), the microcontroller 142 generates a signal on pin 17, called a recharge signal, that drives transistor Q3 to activate an audible alarm device, such as buzzer 147. The buzzer 147 generates an audible sound which indicates that the relative humidity of the gas in the heater/humidifier has dropped below the predetermined threshold and that it is necessary to recharge the heater/humidifier with liquid. In one embodiment, the predetermined relative humidity threshold corresponds to a minimum level for a desirable relative humidity range of the gas exiting the heater/humidifier, and may be 40%, for example. In a further example, the predetermined relative humidity threshold may be 20%, 25%, 30%, 35%, 50%, 60%, 70%, 75%, 80%, 85%, 90%, 95%, or any other suitable percentage of relative humidity. The predetermined relative humidity threshold may be an adjustable or programmable parameter in the microcontroller 142. Optionally, the microcontroller 142 may generate another warning signal at the output of pin 7 to illuminate an light emitting diode (LED) 148A, thereby providing a visual indication of the humidity dropping below the predetermined relative humidity threshold in the heater/humidifier, and the need to recharge the heater/humidifier 120 with liquid. In a further embodiment, the microcontroller 142 generates a trouble or warning signal output at pin 6 to drive LED 148B (of a different color than LED 148A, for example) when there is either a "code fault" in the microcontroller 142 (an extremely unlikely occurrence) or when the relative humidity of the gas in the heater/humidifier is less than a critical relative humidity threshold (lower than the predetermined relative humidity threshold), such as 10%, or any other relative humidity percentage that is lower than the predetermined relative humidity threshold. In either case, power to the heating element 134 may be terminated in response to the warning signal.

In one embodiment, the microcontroller 142 also controls the heating element 134 in order to regulate the temperature of the gas inside the heater/humidifier. Accordingly, the microcontroller 142 processes the digital word supplied by the A/D converter 143 to determine the temperature of the gas inside the heater/humidifier housing. In response, the microcontroller 142 generates a heat control signal on the output pin 11 that drives transistor Q1, which in turn drives the MOSFET power transistor Q2, that supplies current to the heating element 134. The temperature of the gas inside the heater/humidifier may be regulated by the microcontroller 142 so that it is within a temperature range as it exits the heater/humidifier for delivery adjacent to or into the open surgical site. In one embodiment, the temperature range that the gas is regulated to is approximately 35°-40° C. For example, the gas may be regulated to a predetermined temperature set point, such as, 37° C., resulting in a smaller temperature range. Other set points could be used without departing from the scope of the invention. Regulating to a set point may result in a temperature range at the exit of the chamber. In another embodiment, the temperature that the gas is regulated to may be below 35° C. In a further embodiment, the temperature that the gas is regulated to may be above 40° C. In particular embodiments, the temperature range that the gas is regulated to may be approximately 28°-33° C., 30°-35° C., 32%37° C., 37%42° C., 39°-44° C., or any other suitable temperature range. In some embodiments, the temperature may be adjustable and in others it may not. The temperature of the gas may not always be within the temperature range. Changes in flow conditions, start up, or other circumstances may lead to periods where the gas temperature is outside of a desirable range.

As mentioned above, when the relative humidity inside the heater/humidifier falls below a critical threshold as determined by the monitoring circuit portion of the control module 140, the control circuit portion in response terminates power to the heating element 134 to prevent the delivery of warm gas that is extremely dry. The temperature of the gas may not always be within the temperature range. Changes in flow conditions, start up, or other circumstances may lead to periods where the gas temperature is outside of a desirable range.

In one embodiment, the circuitry for monitoring the relative humidity of the gas can be embodied by other circuitry well known in the art. In addition, while the control module 140 has been described as having a single microcontroller 142 for monitoring signals representing temperature and relative humidity of the gas exiting the chamber, and for controlling the heating element to control the temperature of the gas, it should be understood that two or more microcontrollers could be used. For example, one microcontroller may dedicated to each of the individual functions. In addition, the functions of the microcontroller 142 could be achieved by other circuits, such as an application specific integrated circuit (ASIC), digital logic circuits, a microprocessor, a digital signal processor, or any other suitable circuit.

In one embodiment, the volume of gas that can be conditioned with a full supply of liquid in the heater/humidifier may depend on the flow rate and pressure used during a procedure. In particular embodiments, the apparatus may be designed to accommodate different anticipated needs for particular procedures. As an example, the chamber of the heater/humidifier may be designed to hold 8 to 10 cc of liquid that can humidify 180 liters of gas at a relative humidity level of 80% or more. The microcontroller 142 is programmable to issue the recharge signal when the humidity of the gas drops below the predetermined relativity humidity threshold, independent of the flow rate or pressure of the insufflation gas supply. Preferably, the predetermined relativity humidity threshold is set so that brief periods of high pressure or high flow rate do not cause this threshold to be triggered, because the humidity level will return to greater-than-threshold levels shortly after the high pressure/flow rate periods ends.

Modifications, additions, or omissions may be made to the control module 140 without departing from the scope of the invention. The components of the control module 140 may be integrated or separated. Moreover, the operations of the control module 140 may be performed by more, fewer, or other components. For example, the operations of the microcontroller 142 may be performed by more than one component.

Figure 9:
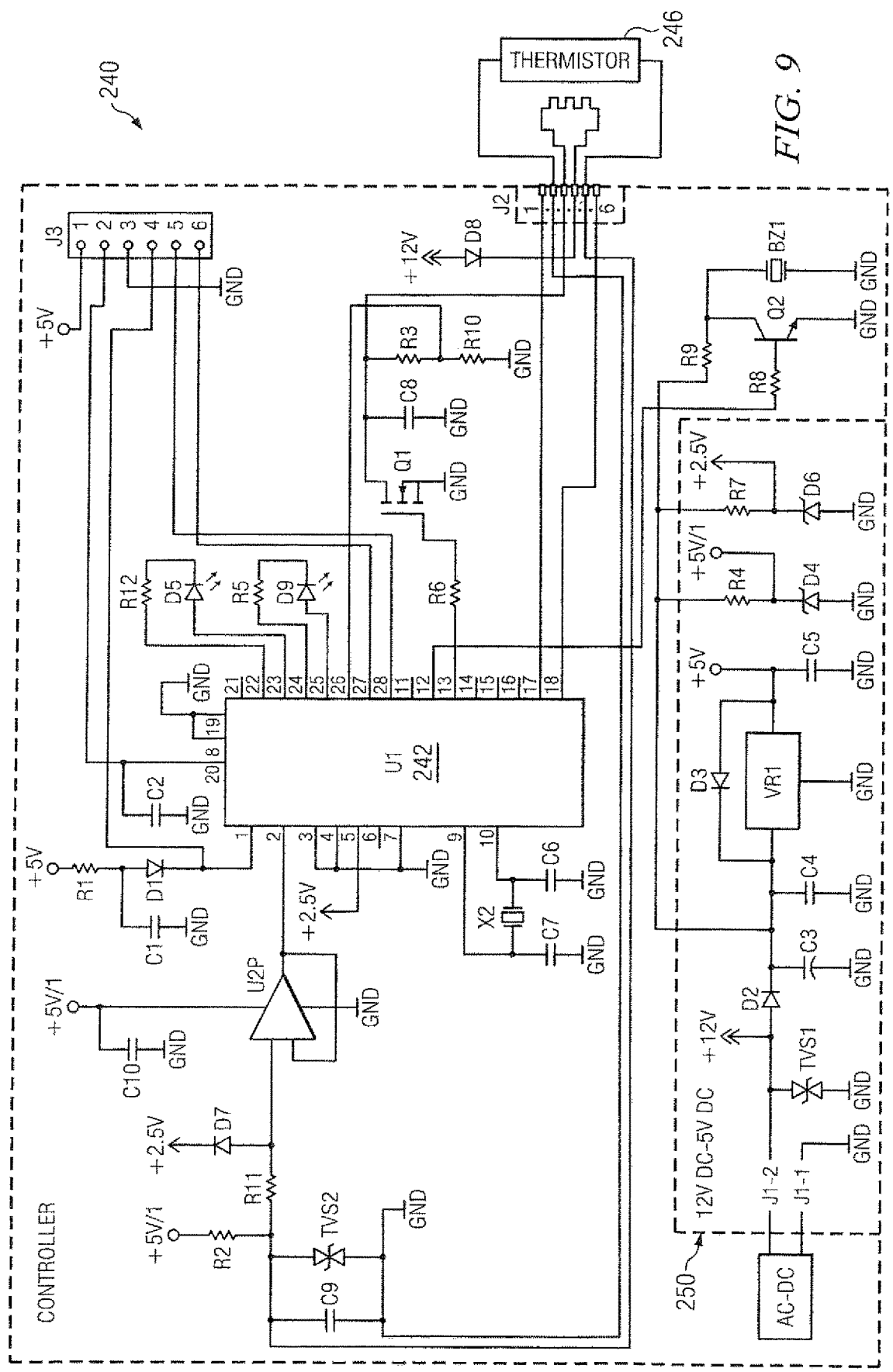
FIG. 9 is a schematic diagram showing a further embodiment of a control circuit of an apparatus that may be used in a surgical method.

In a further embodiment, other various control modules may be used in the apparatus 100 instead of the control module 140 of FIG. 8. For example, FIG. 9 illustrates a control module 240 that may be used in the apparatus 100. In one embodiment, several components of the control module 240 may be located within the electrical housing 210 (FIG. 4), whereas other components may be located within the housing of the heater/humidifier 120 (FIG. 5). However, any location arrangement of the components is allowable.

In one embodiment, the microprocessor 242 is a PIC16F873SO microprocessor that controls the operation of the apparatus 100. The microprocessor 242 receives a 5 V DC from a voltage divider. A clock signal is generated by a 4 MHz resonator X2 tied to pins 9 and 10. An audible buzzer BZ1 whose frequency is determined by a transistor Q2 and two visible LED lights D5 and D9 are controlled by the microprocessor 242 to signal warnings or signal shutdown of the apparatus 100 due to fault conditions that the software scans for.

The microprocessor 242 also controls a heater (not shown), such as a resistive heater, in order to regulate the temperature of the gas inside the heater/humidifier. The heater is activated by pin 13 of the microprocessor 242 that triggers a transistor Q1 to allow a path to ground, completing a 12 V DC circuit. Temperature feedback is provided through pin 27 to the microprocessor 242. Regulation of the temperature by the microprocessor 242 may be software driven. In one embodiment, any suitable software may be used. Furthermore, additional programming of the control module 240 may occur at a programming unit J3. According to the illustrated embodiment, a proportional-integral-derivative (PID) temperature control loop may also be utilized in order to regulate the temperature.

In order to regulate the temperature, the microprocessor 242 receives imbedded temperature feedback from a temperature sensor (thermistor) 246. For example, a temperature sensing loop in the control module 240 may utilize a 5 V DC signal from a voltage divider. This signal is linked to the temperature sensor 246, and is fed to the positive input on an operational amplifier (op amp) U2P. One or more capacitors and one or more resistors may be used to stabilize the signal and reduce the chance of "noise." The amplified signal is then fed to input 2 on the microprocessor 242.

The temperature sensor 246 may be placed in the gas stream. In one embodiment, the temperature sensor 246 may be placed in a location where it does not contact a humidification means of the apparatus 100. The temperature sensor 246 (and the heater) may be connected to the control module 240 via insulated wire and one or more connectors. In the illustrated embodiment, the temperature sensor 246 is connected to the control module 240 at J2 (pins 2 and 5), and the heater is connected to the control module 240 at J2 (pins 3 and 4).

The control module 240 may further include a 120 V AC to 12 V DC converter (power supply). This allows for the control module 240 to utilize standard 120 V AC wall power while using lower/safer voltage 12 V DC for warming. Power is further limited by a voltage regulating circuit 250. For example, the voltage regulating circuit 250 regulates the 12 V DC to a lower voltage, such as 5 V DC, for use by the temperature sensing circuit and the microprocessor 242.

Although FIG. 9 does not illustrate a humidity sensor, any suitable humidity sensor, such as the humidity sensor (and the related humidity sensing/monitoring components) discussed above in FIG. 8, may be used in conjunction with the control module 240 of FIG. 9. Furthermore, the circuitry for monitoring the relative humidity of the gas can be embodied by other circuitry well known in the art. In another embodiment, FIG. 9 may not include a humidity sensor and/or may not include circuitry for monitoring the relative humidity of the gas. Furthermore, while the control module 240 has been described as having a single microprocessor 242 for monitoring signals representing temperature and for controlling the heating element to regulate the temperature of the gas, it should be understood that two or more microprocessors could be used. For example, one microprocessor may dedicated to each of the individual functions. In addition, the functions of the microprocessor 242 could be achieved by other circuits.

Modifications, additions, or omissions may be made to the control module 240 without departing from the scope of the invention. The components of the control module 240 may be integrated or separated. Moreover, the operations of the control module 240 may be performed by more, fewer, or other components. For example, the operations of the microprocessor 242 may be performed by more than one component.

With reference to FIGS. 3 and 4, one embodiment of the setup and operation of the apparatus 100 will be described. The AC/DC converter 180 is plugged into a 110 V AC power source, such as a wall outlet or a power strip. The control module 140 is connected to the AC/DC converter 180. In another embodiment, the apparatus 100 may be powered by a battery or photovoltaic source. The heater/humidifying tubing set is then installed by attaching one end of the tube segment 160 to the outlet of the insufflator 104 by the Luer lock 166. The tube segments 160, 162 and 164 may be pre-attached to the filter 110 and the heater/humidifier 120 for commercial distribution of the apparatus 100. The cable 170 is installed into the electrical housing 210 of control module 140 by the connector 172. The heater/humidifier 120 is charged with a supply of liquid by the syringe 200. For example, 8 cc of a liquid, such as sterile water or saline, is drawn into the syringe 200. The syringe 200 is then inserted into the charging port 190 so that a needle or cannula of the syringe 200 penetrates the resealable member 194 (FIG. 5) and the liquid is injected into the heater/humidifier 120 to be absorbed by the liquid-retaining layers. The syringe 200 is then removed from the charging port 190, and the charging port 190 seals itself. The free end of the tube segment 164 is attached to a gas delivery device, such as one of the non-porous gas delivery mechanisms discussed with regard to FIGS. 2A-2C and/or FIGS. 2D-2E, or any other non-porous gas delivery mechanism, by the Luer lock 168 or other appropriate connector. In another embodiment, the heater/humidifier 120 may be pre-charged with liquid, thus not requiring a charge prior to operation.

Once the insufflator 104 is activated, it receives gas from a gas supply cylinder and regulates the pressure and flow rate of the gas, both of which can be adjusted by the operator. The pressure and volumetric flow rate are controlled by adjusting controls (not shown) on the insufflator 104. Insufflator gas then flows through the tube segment 160 into the optional filter 110 where it is filtered, and then through tube segment 162 into the heater/humidifier 120. In the heater/humidifier 120, gas comes into contact with electrical heating element 134 and the humidifying liquid-retaining layer(s) 130-132 which are positioned within the flow path of the gas, as shown in FIG. 5. In one embodiment, the gas may pass through the humidifying liquid-retaining layer(s) 130-132. In another embodiment, some of the gas may pass through the humidifying liquid-retaining layer(s) 130-132, and/or some of the gas may pass over/under/around the humidifying liquid-retaining layer(s) 130-132. In chamber 128, insufflator gas may be simultaneously humidified and warmed to a desired physiological range by regulation of the heating element 134 and liquid content of the liquid-retaining layers 130-132 such that the temperature of gas exiting chamber 128 is within a desirable physiological temperature range (for example, 35° to 40° C., though any desired temperature range can be predetermined (or preselected), as is discussed above), and within a predetermined (or preselected) range of relative humidity. In one embodiment, the gas may be humidified so that it is within a range of relative humidity at the exit of the heater/humidifier for delivery adjacent to or into the open surgical site. It may also be within any of the following humidity ranges as the gas enters the patient through the exit of a delivery device. The relative humidity level may be above 40%, above 50%, above 60%, above 70%, above 75%, above 80%, above 85%, or above 90% relative humidity. In further embodiments, the range of relative humidity may be between 65-80%, between 70-85%, between 75-90%, between 80-95%, or any other suitable range. In some embodiments, the relative humidity may be between 95% and 100%. In one embodiment, if the apparatus is operated with the heater/humidifier 120 not charged with liquid either because the user forgot to manually charge it before initiating operation, or the apparatus was sold without a pre-charge of liquid (e.g., in a dry state), the relative humidity of the gas in the chamber of the heater/humidifier 120 will be detected to be below the predetermined threshold and the alarm will be activated, alerting the user that the heater/humidifier 120 requires charging of liquid. In one embodiment, the apparatus will automatically issue an alarm to alert a user to the need for charging the heater/humidifier 120 with liquid, thereby avoiding further delivery of unhumidified gas adjacent to or into the open surgical site of the patient.

With further reference to FIG. 8, the control module 140 monitors the relative humidity of the gas exiting the chamber and further regulates the temperature of the gas in the chamber 128. In particular, the microcontroller 142 generates a recharge signal when the relative humidity of the gas in the chamber drops below the predetermined relative humidity threshold, indicating that the liquid supply in the heater/humidifier 120 requires replenishing. An audible alarm is issued by the buzzer 147 and/or a visual alarm is issued by LED 148A to warn the medical attendant or user that the heater/humidifier 120 requires recharging. In one embodiment, the microcontroller 142 continues the alarm until the humidity in the chamber returns to a level above the predetermined relative humidity threshold, which will occur when the heater/humidifier 120 is recharged with liquid. Moreover, the microcontroller 142 will issue a second alarm, such as by energizing LED 148B, when the relative humidity level of gas in the heater/humidifier 120 drops below the critical relative humidity threshold, at which point electrical power to the heating element 134 is terminated. In a further embodiment, the microcontroller 142 controls the temperature of the gas by controlling electrical power supplied to the heating element 134.

In one embodiment, the apparatus of the present disclosure provides for control of the temperature and monitoring of the humidification of the gas, and of particular importance, generates an audible or visual alarm indicating that the heater/humidifier requires recharging of liquid to sustain and provide timed re-supply of liquid in order to maintain a flow of humidified/warmed gas. The alarm is maintained until the heater/humidifier is recharged and the humidity of the gas returns to a predetermined level. In a further embodiment, the apparatus disclosed herein is easily installed and prepared for use with a minimal amount of lines and tubes. The rechargeable feature of the heater/humidifier eliminates the need for an additional liquid supply tube connected to the heater/humidifier. If needed, the heater/humidifier may be recharged with liquid several times during a procedure.

In an additional embodiment, the power supply for the apparatus is derived from a standard AC wall outlet or power strip. Power strips are often provided on medical carts already used in the operating room environment. By using a power supply derived from a (normally) uninterrupted AC source, as opposed to the finite amount of power that can be supplied by a battery, accommodating surgical procedures, such as surgical method 10 of FIG. 1, that last longer than anticipated is not a concern. The control circuitry for the apparatus may be contained in an electrical housing that is relatively movable with respect to the remainder of the apparatus, and therefore can be placed in a non-interfering position in the operating room. For example, the electrical housing of the control module can be attached by tape or Velcro to the side of the insufflator or other stable structure in the operating room, and not encumber the remainder of the apparatus or affect parameter settings of the insufflator.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications.

What is claimed is:

1. A surgical method for performing an open surgical site surgery, comprising:

making an incision in a patient;
opening the incision in order to create an open surgical site in the patient;
receiving a gas from a source;
humidifying and warming the gas received from the source;
flowing the humidified and warmed gas through a non-porous gas delivery mechanism comprising a cup-shaped structure that defines a chamber, the cup-shaped structure having a base, a rim, and a cup-shaped sidewall connecting the base to the rim, wherein the base defines an inlet connecting to an inlet passage of the non-porous gas delivery mechanism, the rim defines an outlet positioned opposite the inlet, and the base has a smaller diameter than the rim, wherein as the humidified and warmed gas flows from the inlet to the outlet of the cup-shaped structure, the humidified and warmed gas is successively reflected off a plurality of non-porous surfaces within the non-porous gas delivery mechanism to create a flow, wherein at least one of the plurality of non-porous surfaces comprises the cup-shaped sidewall, and wherein a second of the plurality of non-porous surfaces is positioned within the chamber defined by the cup-shaped structure and oriented such that it is in a path of the humidified and warmed gas reflected to or from the cup-shaped sidewall of the non-porous gas delivery mechanism;
delivering the flow of the humidified and warmed gas adjacent to or into the open surgical site via the outlet;
receiving condensation created by the humidified and warmed gas; and
directing at least a portion of the condensation through one or more openings in at least one of the plurality of non-porous surfaces.

2. The surgical method of claim 1, further comprising: mechanism, and
delivering at least the portion of the condensation adjacent to or into the open surgical site.

3. The surgical method of claim 1, wherein flowing the humidified and warmed gas through the non-porous gas delivery mechanism comprises:
reflecting the humidified and warmed gas off a first non-porous surface within the non-porous gas delivery mechanism and towards a second non-porous surface within the non-porous gas delivery mechanism; and
reflecting the humidified and warmed gas off the second non-porous surface within the non-porous gas delivery mechanism and towards the outlet of the cup-shaped structure.

4. The surgical method of claim 1, wherein flowing the humidified and warmed gas through the non-porous gas delivery mechanism comprises:
reflecting the humidified and warmed gas off a first non-porous surface within the non-porous gas delivery mechanism and towards a second non-porous surface within the non-porous gas delivery mechanism;
reflecting the humidified and warmed gas off the second non-porous surface within the non-porous gas delivery mechanism and towards a third non-porous surface within the non-porous gas delivery mechanism;
reflecting the humidified and warmed gas off the third non-porous surface within the non-porous gas delivery mechanism and towards a fourth non-porous surface within the non-porous gas delivery mechanism; and reflecting the humidified and warmed gas off the fourth non-porous surface within the non-porous gas delivery mechanism and towards the outlet of the cup-shaped structure.

5. The method of claim 1, wherein at least a portion of each of the plurality of non-porous surfaces positioned within the chamber defined by the cup-shaped structure of the non-porous gas delivery mechanism has an approximately parabolic shape.

6. The surgical method of claim 1, wherein flowing the humidified and warmed gas through the non-porous gas delivery mechanism comprises:
    directing the humidified and warmed gas to a first non-porous surface within the non-porous gas delivery mechanism, the first non-porous surface comprising a first curved surface configured to reflect the humidified and warmed gas to a second non-porous surface within the non-porous gas delivery mechanism, wherein the first non-porous surface comprises a medical grade acrylic material;
    reflecting the humidified and warmed gas off the first non-porous surface and towards the second non-porous surface, the second non-porous surface comprising a second curved surface configured to reflect the humidified and warmed gas towards the outlet of the cup-shaped structure, wherein the second non-porous surface comprises the medical grade acrylic material; and
    reflecting the humidified and warmed gas off the second non-porous surface towards the outlet of the cup-shaped structure.

7. The surgical method of claim 1, wherein flowing the humidified and warmed gas through the non-porous gas delivery mechanism comprises successively reflecting the humidified and warmed gas off the plurality of non-porous surfaces within the non-porous gas delivery mechanism to create a laminar or substantially laminar flow.

8. The method of claim 1, wherein the humidifying and warming the gas received from the source comprises passing the gas through a chamber comprising a volume of a liquid.

9. The method of claim 8, wherein the liquid comprises sterile water and the liquid further comprises one or more anesthetics or one or more anticoagulants.

10. The method of claim 8, further comprising injecting an additional amount of the liquid into the chamber.

11. The method of claim 8, wherein the volume of the liquid is contained in an absorbent material.

12. The method of claim 8, wherein the volume of the liquid is maintained between two or more membranes.

13. The method of claim 1, wherein the second of the plurality of non-porous surfaces comprises a parabolic structure having a concave surface facing the inlet of the cup-shaped structure and a convex surface facing the outlet of the cup-shaped structure.

14. The method of claim 1, wherein the second of the plurality of non-porous surfaces comprises a conical structure.

15. The method of claim 1, wherein the humidifying and warming the gas received from the source comprises increasing a humidity of the gas to a range of 80% through 95% relative humidity.

16. The method of claim 1, wherein the humidifying and warming the gas received from the source comprises increasing a humidity of the gas to above 40% relative humidity.

17. The method of claim 1, wherein the humidifying and warming the gas received from the source comprises increasing a humidity of the gas to above 60% relative humidity.

18. The method of claim 1, wherein the humidifying and warming the gas received from the source comprises increasing a humidity of the gas to above 80% relative humidity.

19. The method of claim 1, wherein the humidifying and warming the gas received from the source comprises increasing a humidity of the gas to above 90% relative humidity.

20. The method of claim 1, wherein the humidifying and warming the gas received from the source comprises increasing a humidity of the gas to above 95% relative humidity.

21. The method of claim 1, wherein the gas comprises carbon dioxide.

22. The method of claim 1, further comprising filtering the gas received from the source.

23. The method of claim 1, further comprising monitoring a relative humidity of the humidified and warmed gas delivered into the open surgical site.

24. The method of claim 1, further comprising:
    coupling the non-porous gas delivery mechanism to an adjustable arm support; and
    positioning, using the adjustable arm support, the non-porous gas delivery mechanism outside of the open surgical site.

25. The method of claim 1, wherein the second of the plurality of non-porous surfaces comprises a conical structure and at least a portion of the conical structure extends into the inlet passage of the non-porous gas delivery mechanism.

26. The method of claim 1, wherein:
    the second of the plurality of non-porous surfaces comprises a first parabolic structure and a first of the one or more openings is located at a vertex of the first parabolic structure; and
    a third of the plurality of non-porous surfaces comprises a second parabolic structure and a second of the one or more openings is located at a vertex of the second parabolic structure;
    wherein the first opening and the second opening are each in alignment with a central axis that extends through the inlet passage of the non-porous gas delivery mechanism.

* * * * *